(12) United States Patent
Chen et al.

(10) Patent No.: US 12,005,432 B2
(45) Date of Patent: Jun. 11, 2024

(54) CONFIGURABLE WORKSTATIONS

(71) Applicant: CooperSurgical, Inc., Trumbull, CT (US)

(72) Inventors: Shuo Robert Chen, White Plains, NY (US); Rodrigo DaSilva, Waterbury, CT (US); Wilfrido Enrique Thalliens Angulo, Cornwall (GB); Adam H Morales, Trumbull, CT (US); Robert Williams, Norwalk, CT (US); Robert Thompson, Cornwall (GB); Luke Thomas Lane, Cornwall (GB); Vagn Rasmussen, Roskilde (DK); Timothy Stanhope, Cornwall (GB)

(73) Assignee: CooperSurgical, Inc., Trumbull, CT (US)

( * ) Notice: Subject to any disclaimer, the term of this patent is extended or adjusted under 35 U.S.C. 154(b) by 917 days.

(21) Appl. No.: 17/065,755

(22) Filed: Oct. 8, 2020

(65) Prior Publication Data
US 2021/0106984 A1 Apr. 15, 2021

Related U.S. Application Data

(60) Provisional application No. 62/913,371, filed on Oct. 10, 2019.

(51) Int. Cl.
*G01N 33/68* (2006.01)
*B01L 1/00* (2006.01)
(Continued)

(52) U.S. Cl.
CPC .............. *B01L 1/00* (2013.01); *G05B 19/042* (2013.01); *G06K 7/10297* (2013.01);
(Continued)

(58) Field of Classification Search
CPC ................ B01L 1/00; B01L 2200/028; B01L 2200/0684; B01L 2200/0689;
(Continued)

(56) References Cited

U.S. PATENT DOCUMENTS 7,028,913 B2    4/2006 Reinhardt et al.
7,712,847 B1    5/2010 Albright et al.
(Continued)

FOREIGN PATENT DOCUMENTS

| EP | 1609541 A2 * | 12/2005 | ................ B01L 1/50 |
| EP | 3 109 641 | 12/2016 | ............. G01N 35/00 |

(Continued)

OTHER PUBLICATIONS

The International Search Report and the Written Opinion of the International Searching Authority for International Application No. PCT/US2020/054782 dated Mar. 9, 2021.
(Continued)

*Primary Examiner* — Jennifer Wecker
*Assistant Examiner* — Oyeleye Alexander Alabi
(74) *Attorney, Agent, or Firm* — Fish & Richardson P.C.

(57) ABSTRACT

A configurable workstation includes a support frame defining a workspace for performing a scientific procedure, multiple modules that are configured to be selectively installed to the support frame for customizing a functional profile of the configurable workstation, and a server computing device hosting an application that provides a user interface for controlling operations of the configurable workstation.

40 Claims, 32 Drawing Sheets

(51) Int. Cl.
*B01L 3/00* (2006.01)
*C07C 309/65* (2006.01)
*C07C 309/73* (2006.01)
*C12M 1/26* (2006.01)
*C12M 3/06* (2006.01)
*G01N 21/33* (2006.01)
*G01N 21/64* (2006.01)
*G01N 33/52* (2006.01)
*G05B 19/042* (2006.01)
*G06K 7/10* (2006.01)
*G16H 10/40* (2018.01)
*G16H 40/20* (2018.01)
*G16H 40/40* (2018.01)
*G16H 40/63* (2018.01)
*H04L 67/10* (2022.01)
*H04L 67/12* (2022.01)

(52) U.S. Cl.
CPC ............ *G16H 10/40* (2018.01); *G16H 40/20* (2018.01); *G16H 40/40* (2018.01); *G16H 40/63* (2018.01); *B01L 2200/028* (2013.01); *B01L 2200/0684* (2013.01); *B01L 2200/0689* (2013.01); *B01L 2300/0681* (2013.01); *B01L 2300/1805* (2013.01); *B01L 2300/1844* (2013.01); *B01L 2300/1894* (2013.01); *G05B 2219/2614* (2013.01); *H04L 67/10* (2013.01); *H04L 67/12* (2013.01)

(58) Field of Classification Search
CPC ..... B01L 2300/0681; B01L 2300/1805; B01L 2300/1844; B01L 2300/1894; B01L 1/04; G05B 19/042; G05B 2219/2614; G06K 7/10297; G16H 10/40; G16H 40/20; G16H 40/40; G16H 40/63; H04L 67/10; H04L 67/12
See application file for complete search history.

(56) References Cited

U.S. PATENT DOCUMENTS

| | | | |
|---|---|---|---|
| 9,055,812 | B2 | 6/2015 | Fishman et al. |
| 9,060,598 | B2 | 6/2015 | Isgro |
| 9,516,944 | B2 | 12/2016 | Lawrence |
| 9,732,314 | B2 | 8/2017 | Shibata et al. |
| 10,226,120 | B2 | 3/2019 | Chau |
| 10,307,802 | B2 | 6/2019 | Ross et al. |
| 2009/0020442 | A1* | 1/2009 | Dietrich .............. G06K 7/0008 206/232 |
| 2010/0151564 | A1 | 6/2010 | Beebe et al. |
| 2014/0087455 | A1* | 3/2014 | Kobayashi ............. C12M 41/14 435/294.1 |
| 2017/0023561 | A1* | 1/2017 | Martinell Gispert-Sauch ............. G01N 35/00722 |
| 2018/0002649 | A1 | 1/2018 | Pedersen |
| 2019/0308195 | A1 | 10/2019 | Meier et al. |
| 2019/0376012 | A1 | 12/2019 | Pedersen |
| 2019/0377370 | A1 | 12/2019 | Schuck et al. |
| 2021/0155978 | A1* | 5/2021 | Tidd ..................... C12Q 1/6844 |

FOREIGN PATENT DOCUMENTS

| | | | | |
|---|---|---|---|---|
| GB | 2501283 A | * | 10/2013 | ............... B01L 1/04 |
| WO | WO-1990005549 A1 | * | 5/1990 | |
| WO | WO 2019/014239 | | 1/2019 | ............. B01J 19/00 |
| WO | WO 2019/103225 | | 5/2019 | |
| WO | WO 2019/207892 | | 10/2019 | |

OTHER PUBLICATIONS

The International Preliminary Report on Patentability for International Application No. PCT/US2020/054782, dated Apr. 21, 2022.

* cited by examiner

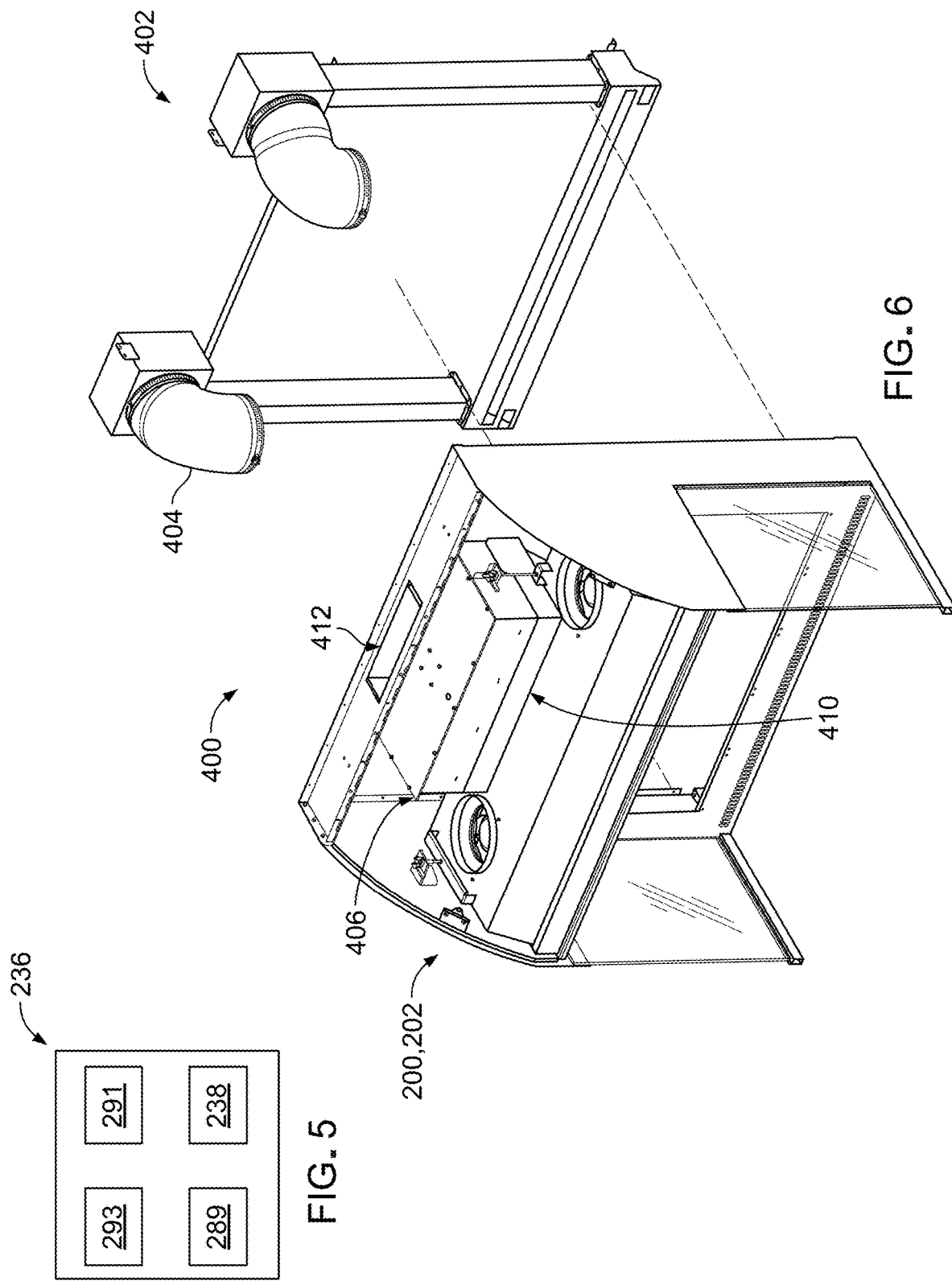

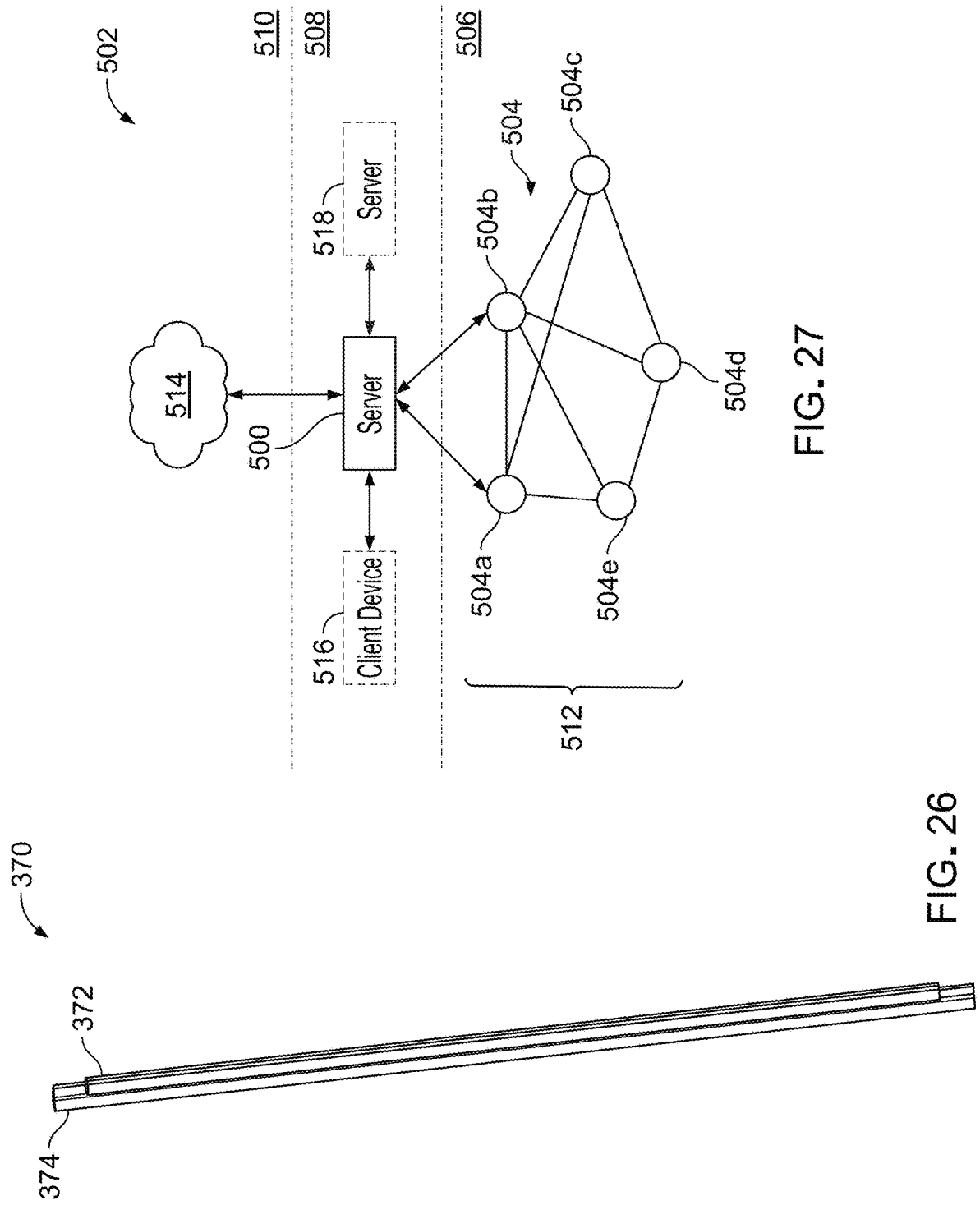

CONFIGURABLE WORKSTATIONS

CROSS-REFERENCE TO RELATED APPLICATIONS

This application claims priority to U.S. Provisional Patent Application No. 62/913,371, filed on Oct. 10, 2019. The entire content of this application is incorporated herein by reference.

TECHNICAL FIELD

This disclosure relates to configurable workstations, such as modularized workstations that are configurable on-site at laboratories for carrying out biological protocols.

BACKGROUND

Biosafety cabinets and laminar flow workstations provide a workspace for carrying out various biological protocols, such as protocols for carrying out in vitro fertilization (IVF) and other biological procedures. Biosafety cabinets and laminar flow workstations are generally configured with a specific design that meets a customer's requirements. As a result of advanced training, expertise, and dexterity required to perform IVF procedures, embryologists in different laboratories typically have specific requirements for layouts of work areas in order to perform the procedures easily and most efficiently. Such requirements drive a large variety of configurations and versions of biosafety cabinets and laminar flow workstations, which leads to high costs of maintaining such products and high costs of controlling product quality. Furthermore, while equipment technologies for IVF are advancing rapidly, such new technologies cannot be easily integrated into the small the workspaces of existing biosafety cabinets and laminar flow workstations.

SUMMARY

In general, this disclosure relates to configurable workstations (e.g., biosafety cabinets) for carrying out biological protocols (e.g., IVF protocols) in a laboratory environment. The configurable workstations are networked systems with a modularized design that is customizable on-site at a laboratory to meet various environmental and functional requirements. The configurable workstations are also networked systems that provide regulatory independence for system sub-components of different regulatory classes.

In one aspect, a configurable workstation includes a support frame defining a workspace for performing a scientific procedure, multiple modules that are configured to be selectively installed to the support frame for customizing a functional profile of the configurable workstation, an air duct system that is configured to be selectively installed to the support frame for changing an airflow path at the configurable workstation, and a server computing device hosting an application that provides a user interface for controlling operations of the configurable workstation.

Embodiments may include one or more of the following features.

In some embodiments, the multiple modules include multiple table-top modules that are configured to be oriented horizontally at the support frame and multiple wall modules that are configured to be oriented vertically at the support frame.

In some embodiments, the support frame includes a table at which one or more table-top modules of the multiple table-top modules can be selectively installed to provide a substantially flat work surface at the workspace and a wall at which one or more wall modules of the multiple wall modules can be selectively installed to define a vertical boundary of the workspace.

In some embodiments, the table includes a platform defining an opening sized to receive the one or more table-top modules and rails to which the one or more table-top modules are attachable for installation to the frame.

In some embodiments, each table-top module of the multiple table-top modules includes a housing that is attachable to the rails, and the table-top module is equipped with a pulling mechanism for pulling the table-top module downward towards the rails to lock the table-top module in a lateral position at the table.

In some embodiments, the table-top module is further equipped with a pushing mechanism for pushing the table-top module up away from the rails to level the table-top module with respect to the platform and any adjacent table-top modules installed at the table to provide the flat work surface.

In some embodiments, the table-top module is further equipped with an adjustment block along a lateral edge of the housing by which the table-top module and an adjacent module are pulled together to minimize a gap between the table-top module and the adjacent table-top module.

In some embodiments, the adjustment block is configured to permit vertical adjustment of the lateral edge of the housing with respect to the adjacent table-top module.

In some embodiments, the configurable workstation further includes a gasket that is configured to seal the gap between the table-top module and the adjacent table-top module.

In some embodiments, the wall defines an opening sized to receive the one or more wall modules.

In some embodiments, the configurable workstation further includes a gasket that is configured to seal a gap between adjacent wall modules of the one or more wall modules installed at the vertical opening.

In some embodiments, the multiple table-top modules include one or more of an anti-vibration platform, an incubator, a cooling unit, one or more heating plates, and a blank table platform.

In some embodiments, the multiple wall modules include one or more of a humidifier, an ICSI arch, a wall tunnel, one or more monitors, a power outlet panel, and a blank wall panel.

In some embodiments, one or more of the multiple modules include an RFID capability for tracking a specimen handled at the workstation.

In some embodiments, the support frame and the multiple modules include multiple medical devices that are subject to regulatory review.

In some embodiments, each medical device of the multiple medical devices includes equipment for carrying out a dedicated medical function, a power port, hardware, firmware, a user interface, and a network communication board for communicating with the server computing device.

In some embodiments, the multiple medical devices are configured to communicate with each other and with the server computing device via a network.

In some embodiments, the network is a mesh network.

In some embodiments, each medical device of the multiple medical devices is configured to be powered and operated independently of other medical devices of the multiple medical devices.

In some embodiments, the support frame includes a table providing a work surface at the workspace and a wall defining a vertical boundary of the workspace.

In some embodiments, the table includes a platform defining multiple horizontal openings along a front edge of the platform and an air duct positioned underneath the platform.

In some embodiments, the wall defines multiple vertical openings adjacent a rear edge of the platform.

In some embodiments, the air duct is in fluid communication with the multiple horizontal openings and the multiple vertical openings.

In some embodiments, the air duct extends from the front edge of the platform along lateral sides of the support frame to the wall.

In some embodiments, the configurable workstation further includes one or more fans disposed above the workspace and configured to circulate air downward into the workspace and a filter disposed beneath the one or more fans for filtering the air that flows from the one or more fans.

In some embodiments, the air duct system includes a duct frame that is configured to be installed to the support frame adjacent the wall, sealed to the air duct of the table, and sealed to the one or more fans disposed above the workspace to define a recirculation airflow path at the support frame.

In some embodiments, the configurable workstation is configured to flow air along the recirculation airflow path downward from the one or more fans, into the workspace, underneath the table along lateral sides of the support frame and rearwardly through the wall, upwardly behind the wall, and back to the one or more fans.

In some embodiments, the air duct system further includes an exhaust fan and a vent for exhausting air from an interior region of the support frame to an ambient environment.

In some embodiments, the air duct system is removable from the support frame to allow air to be circulated downward into the workspace by the one or more fans along a flow-through airflow path.

In some embodiments, the air duct is slidable towards the frame to place the air duct in fluid communication with the multiple horizontal openings on the platform.

In some embodiments, the air duct is removable from the platform for cleaning the air duct.

In some embodiments, the platform is pivotable upward from the air duct for cleaning the air duct.

In some embodiments, the support frame includes an upper panel structure that defines the workspace, a lower panel structure that supports the upper panel structure, and a table that extends intermediately between the upper and lower panel structures and that provides a work surface at the workspace.

In some embodiments, the upper panel structure is configured to support one or more of the multiple wall modules, and the table is configured to support one or more of the multiple table-top modules.

In some embodiments, the server computing device is housed at the support frame.

In some embodiments, the server computing device is configured to communicate with one or more client devices and one or more local servers via a LAN.

In some embodiments, the server computing device is configured to communicate with one or more remote devices on a cloud network via an external network.

In some embodiments, the configurable workstation is convertible between a Class II biosafety cabinet and a Class I laminar flow cabinet.

In some embodiments, the scientific procedure is part of an IVF protocol.

In another aspect, a configurable workstation includes a support frame defining a workspace for performing a scientific procedure, multiple modules that are configured to be selectively installed to the support frame for customizing a functional profile of the configurable workstation, and a server computing device hosting an application that provides a user interface for controlling operations of the configurable workstation.

In some embodiments, the multiple modules include multiple table-top modules that are configured to be oriented horizontally at the support frame and multiple wall modules that are configured to be oriented vertically at the support frame.

In some embodiments, the support frame includes a table at which one or more table-top modules of the multiple table-top modules can be selectively installed to provide a substantially flat work surface at the workspace and a wall at which one or more wall modules of the multiple wall modules can be selectively installed to define a vertical boundary of the workspace.

In some embodiments, the table includes a platform defining an opening sized to receive the one or more table-top modules and rails to which the one or more table-top modules are attachable for installation to the frame.

In some embodiments, each table-top module of the multiple table-top modules includes a housing that is attachable to the rails, and the table-top module is equipped with a pushing mechanism for pushing the table-top module up away from the rails to level the table-top module with respect to the platform and any adjacent table-top modules installed at the table to provide the flat work surface.

In some embodiments, the table-top module is further equipped with a pulling mechanism for pulling the table-top module downward towards the rails to lock the table-top module in a lateral position at the table.

In some embodiments, the configurable workstation further includes a gasket that is configured to seal a gap between the table-top module and an adjacent table-top module.

In some embodiments, the wall defines an opening sized to receive the one or more wall modules.

In some embodiments, the configurable workstation further includes a gasket that is configured to seal a gap between adjacent wall modules of the one or more wall modules installed at the vertical opening.

In some embodiments, the multiple table-top modules include one or more of an anti-vibration platform, an incubator, a cooling unit, one or more heating plates, a microscope module, and a blank table platform.

In some embodiments, the multiple wall modules include one or more of a humidifier, an ICSI arch, a wall tunnel, one or more monitors, a power outlet panel, and a blank wall panel.

In some embodiments, one or more of the multiple modules include an RFID capability for tracking a specimen handled at the workstation.

In some embodiments, the support frame and the multiple modules include multiple medical devices that are subject to regulatory review.

In some embodiments, each medical device of the multiple medical devices include equipment for carrying out a dedicated medical function, a power port, hardware, firmware, a user interface, and a network communication board for communicating with the server computing device.

In some embodiments, the multiple medical devices are configured to communicate with each other and with the server computing device via a network.

In some embodiments, the network comprises a mesh network.

In some embodiments, each medical device of the multiple medical devices is configured to be powered and operated independently of other medical devices of the multiple medical devices.

In some embodiments, the support frame includes a table providing a work surface at the workspace and a wall defining a vertical boundary of the workspace.

In some embodiments, the table includes a platform defining multiple horizontal openings along a front edge of the platform and an air chamber positioned underneath the platform.

In some embodiments, the support frame includes an air duct positioned along a rear edge of the platform, and wherein a gap is defined between the rear edge of the platform and the air duct.

In some embodiments, the air duct is in fluid communication with the multiple horizontal openings and the gap.

In some embodiments, the air duct is a first air duct, and the support frame further includes a second air duct that is positioned above and in fluid communication with the first air duct.

In some embodiments, the configurable workstation further includes one or more fans disposed above the workspace and configured to circulate air downward into the workspace and a filter disposed beneath the one or more fans for filtering the air that flows from the one or more fans.

In some embodiments, the one or more fans include two fans arranged in serial in the air-flow path.

In some embodiments, the configurable workstation is configured to flow air along a recirculation airflow path downward from the one or more fans, into the workspace, underneath the platform of the table, upwardly behind the wall, and back to the one or more fans.

In some embodiments, the configurable workstation further includes one or both of an exhaust fan and a vent for exhausting air from an interior region of the support frame to an ambient environment.

In some embodiments, the configurable workstation further includes an air duct system that is configured to be selectively installed to the support frame for changing an airflow path at the configurable workstation.

In some embodiments, the air duct system is removable from the support frame to allow air to be circulated downward into the workspace by the one or more fans along a flow-through airflow path.

In some embodiments, the configurable workstation is convertible between a Class II biosafety cabinet and a Class I laminar flow cabinet.

In some embodiments, the support frame includes an upper panel structure that defines the workspace, a lower panel structure that supports the upper panel structure, and a table that extends intermediately between the upper and lower panel structures and that provides a work surface at the workspace.

In some embodiments, the upper panel structure is configured to support one or more of the multiple wall modules, and the table is configured to support one or more of the multiple table-top modules.

In some embodiments, the server computing device is housed at the support frame.

In some embodiments, the server computing device is configured to communicate with one or more client devices and one or more local servers via a wired or wireless local area network (LAN).

In some embodiments, the server computing device is configured to communicate with one or more remote devices on a cloud network via an external network.

In some embodiments, the scientific procedure is part of an IVF protocol.

Embodiments may provide one or more of the following advantages.

The configurable workstation has a modularized design that is customizable on-site at a laboratory to meet various laboratory requirements and provide selected functional capabilities. The customizable design of the configurable workstation facilitates upgrading of existing technologies and integration of new technologies at the configurable workstation without replacing the configurable workstation with an entirely new workstation at significant cost and laboratory downtime. For example, by selectively installing desired modules at a workstation frame, a functional profile of the configurable workstation may be customized to provide capabilities required to carry out certain experimental procedures, to meet certain requirements of a laboratory at which the workstation is located, or to identify specimens in a certain manner.

Furthermore, as long as power is supplied to a module at a built-in power port, the modules can operate even without installation to the frame and can perform their intended functionalities without connection to a web application implemented on a server computer of the configurable workstation. In some embodiments, the web application can be accessed to allow the user to control all functions of the frame and the modules from a single location.

The network communication architecture on which the configurable workstation operates alleviates privacy and performance concerns related to handling and storing medical data by supporting the devices (e.g., such as the frame and the modules) on a local network to reduce a chance of unauthorized access to the devices and data stored on or transferred by the devices. The network communication architecture is also flexible to handle a variable number of devices without prior customization at a factory.

The devices can communicate with each other through a local mesh network and with the server computer independently of the other devices such that if one device malfunctions, the operation of the remaining devices will not be hindered or affected. In this manner, the network communication architecture ensures device independence. Not only is independence of the devices important for certain customer needs and technically robust, but such independence advantageously allows independent handling (e.g., access and control) of devices in distinct regulatory classes. Accordingly, a regulatory approval status for one device will not affect a regulatory approval status of another device.

In some embodiments, the configurable workstation defines an airflow path along which air flows laterally, forwardly, and rearwardly at a frame to advantageously avoid contact with certain components of the configurable workstation and a specimen handled in a workspace of the configurable workstation to reduce the likelihood of contaminating the specimen and such components. Furthermore, the configurable workstation is designed such that the airflow path is unaffected by the combination of modules selectively installed at the frame. Independence of the airflow path from the modules advantageously permits factory testing of the airflow path prior to shipment of the configurable workstation to a customer site. Furthermore, an air duct system may be disassembled from the frame of the configurable workstation to convert the configurable workstation from a Class II biosafety cabinet to a Class I laminar flow cabinet, avoiding the need to acquire an entirely new laminar flow cabinet that meets Class I requirements.

DESCRIPTION OF DRAWINGS

FIG. 5 is a schematic illustration of a control module of the configurable workstation of FIG. 1.

FIG. 6 is an exploded view of a portion of an upper panel structure and an air duct frame of the configurable workstation of FIG. 1.

FIG. 26 is a perspective view of a gasket that is installable between adjacent wall modules of FIG. 25.

FIG. 27 is a schematic diagram of a network communication architecture 502 on which the configurable workstation of FIG. 1 operates.

DETAILED DESCRIPTION

Figure 1:
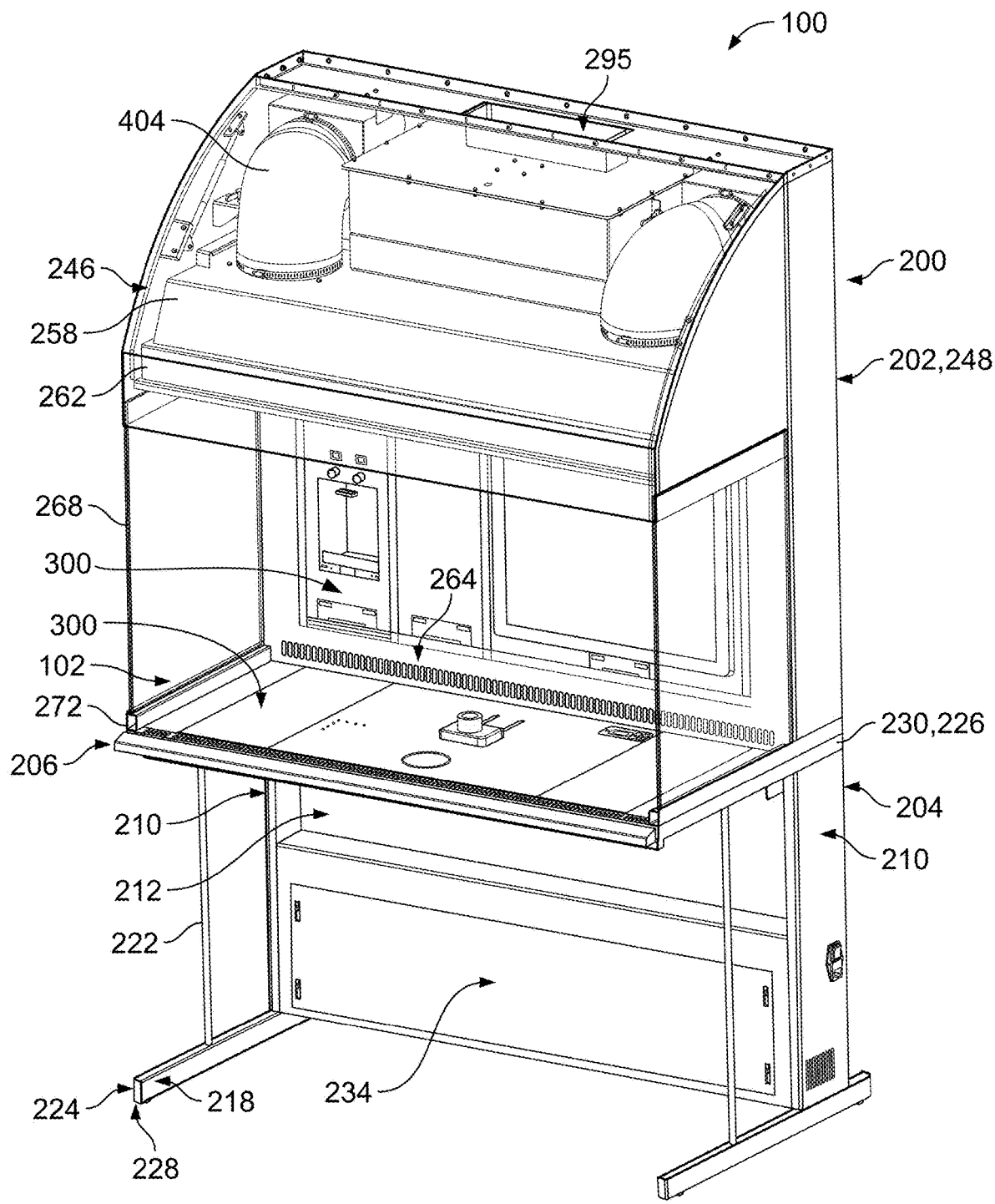
FIG. 1 is a front perspective view of a configurable workstation.
Figure 2:
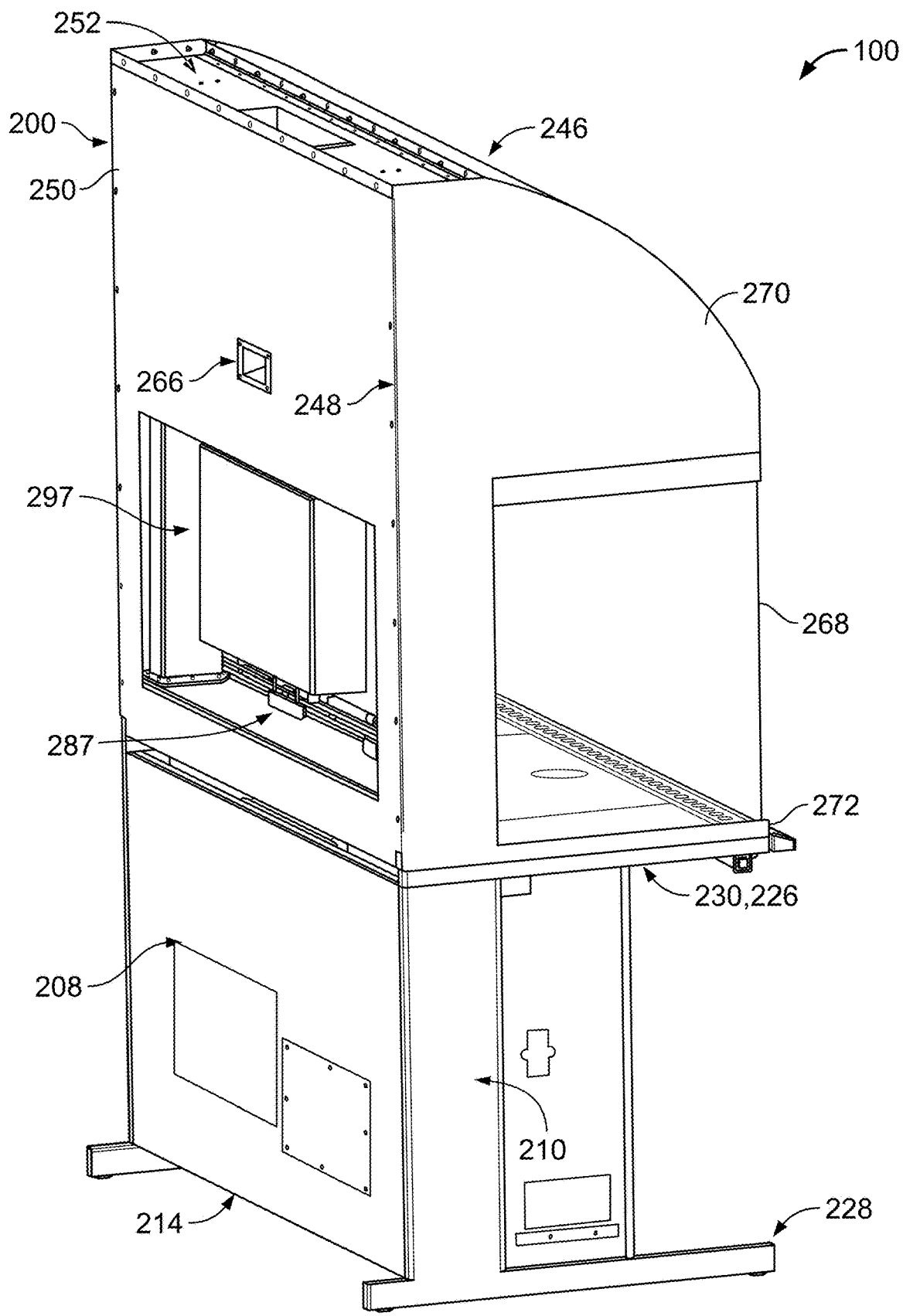
FIG. 2 is a rear perspective view of the configurable workstation of FIG. 1.

FIGS. 1 and 2 illustrate various views of a configurable workstation 100 (e.g., a biosafety cabinet) that provides a workspace 102 for carrying out biological protocols in a laboratory environment. Various biological protocols may be carried out in the workspace 102, such as those related to in vitro fertilization (IVF), cell examination, cell selection, and cell manipulation in the field of assisted reproductive technology (ART). For example, procedures involving one or more of vitrification of specimens, intracytoplasmic sperm injection (ICSI), embryo biopsy, insemination, sperm preparation, and egg selection are typically performed within the workspace 102. Example specimens that are typically handled in the workspace 102 during such procedures include oocytes, blastocysts, embryos, and other animal cells.

The configurable workstation 100 is a networked system with a modularized design that is customizable on-site at a laboratory to meet various laboratory requirements and provide functional capabilities needed to perform selected procedures at the configurable workstation 100. Such requirements may relate to one or more of cost, layout, sterility, airflow patterns, data access, data transfer, sample tracking, work-flow tracking, quality control, temperature control, gas mixture control, incubation, and control of embryo or oocyte environment. The customizable design of the configurable workstation 100 facilitates upgrading of existing technologies and integration of new technologies at the configurable workstation 100 without replacing the configurable workstation 100 with an entirely new workstation at significant cost and laboratory downtime. The customizable design enables easy integration of radio frequency identification (RFID) capabilities for tracking IVF specimens and other specimens. The configurable workstation 100 includes a frame 200, multiple modules 300 that may be selectively installed to the frame 200 as desired for customizing a functional profile of the configurable workstation 100, an air duct system 400 that can be removed from or installed to the frame 200 for modifying an airflow path at the configurable workstation 100, and a server computer 500 that implements a web application to provide a central user interface for communicating with the configurable workstation 100.

The frame 200 is operable to perform clinical functions and is therefore classified as a medical device that is subject to a regulatory review process carried out by a regulatory entity (e.g., the U.S. Food and Drug Administration (FDA) or another regulatory entity). The frame 200 includes an upper panel structure 202, a lower panel structure 204, and a table 206 that extends horizontally from the upper and lower panel structures 202, 204.

Figure 3:
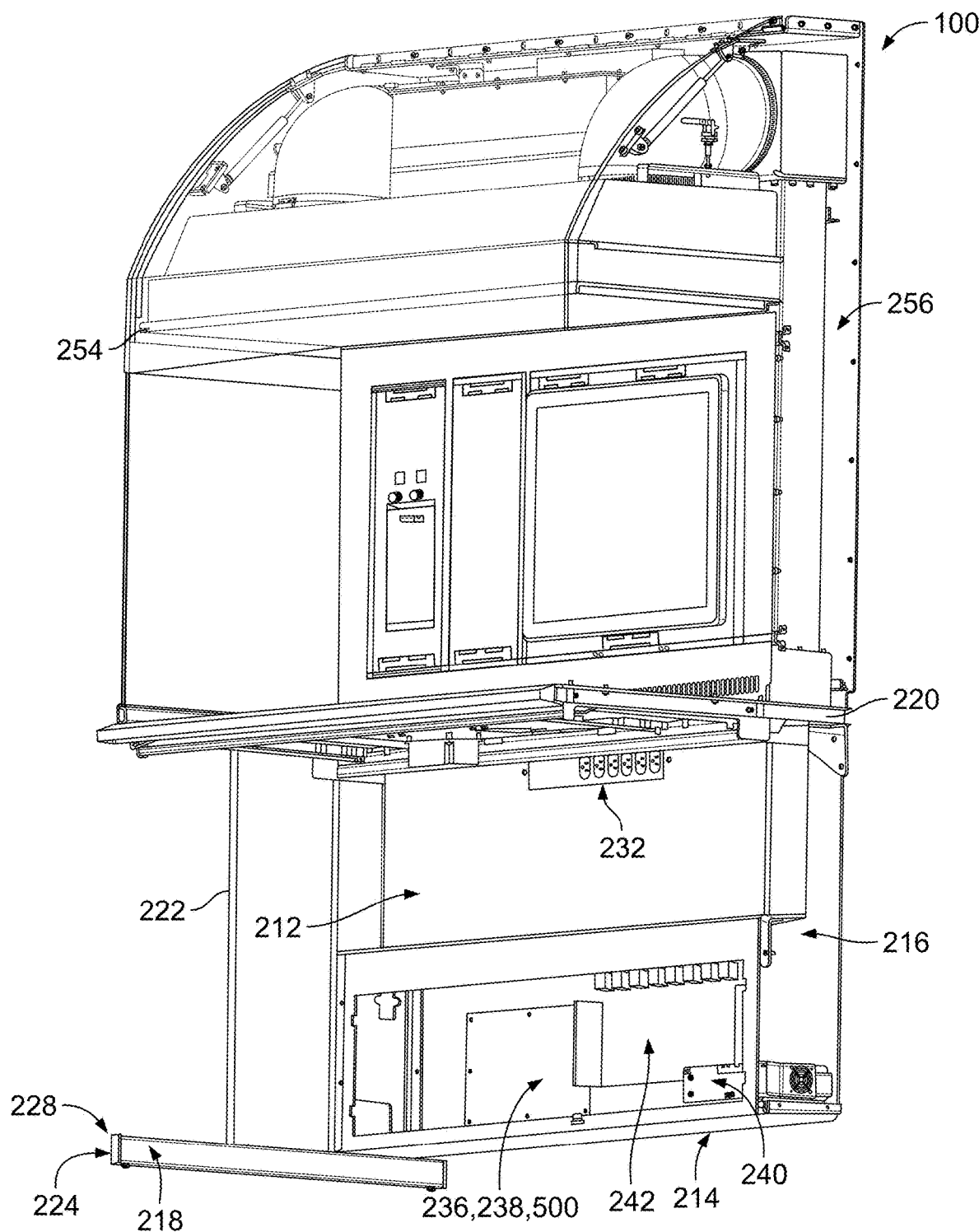
FIG. 3 is a front perspective view of the configurable workstation of FIG. 1 with certain panels of the configurable workstation omitted to expose certain interior components.
Figure 4:
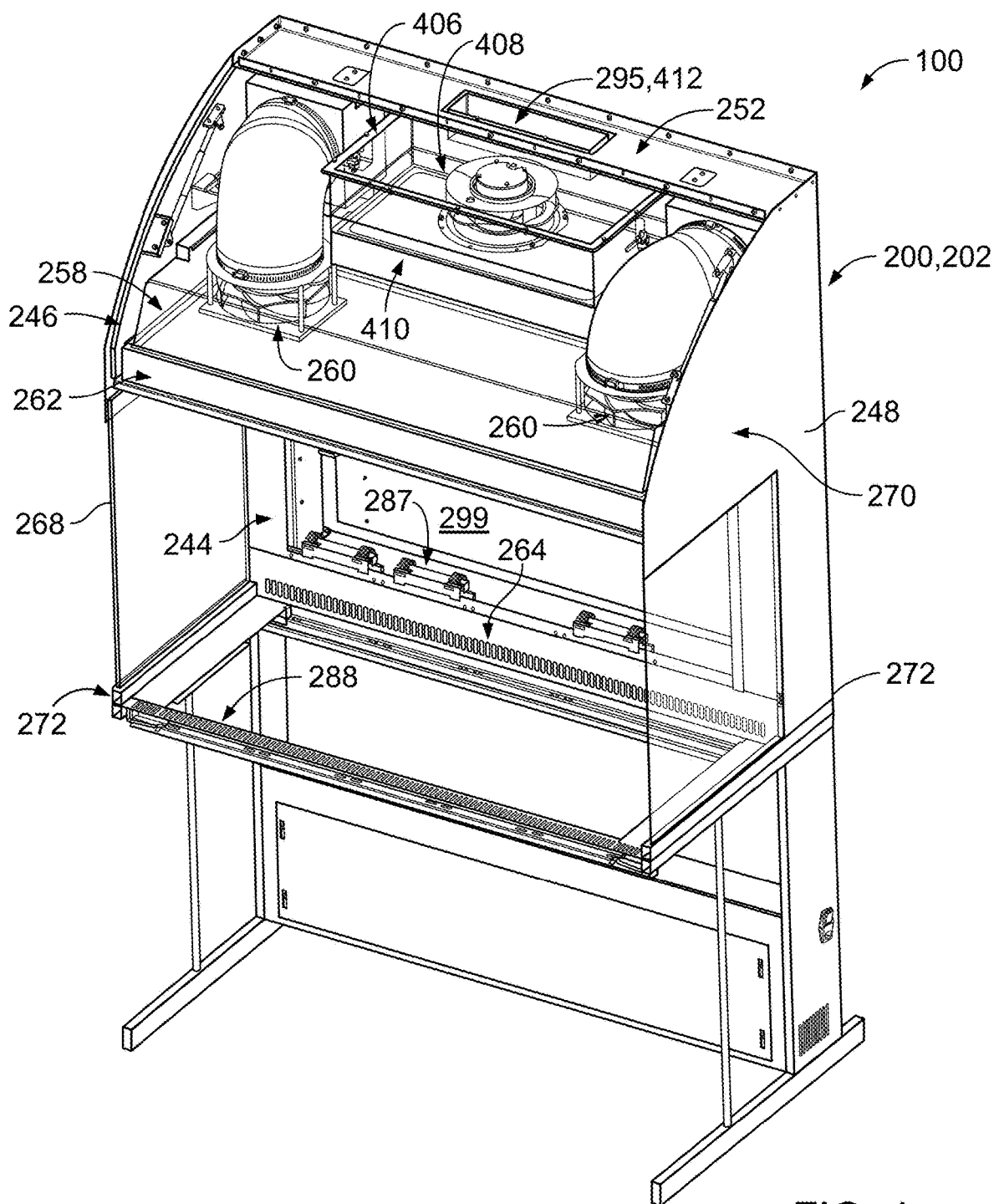
FIG. 4 is a front perspective view of the configurable workstation of FIG. 1 with modules and certain other components of the configurable workstation omitted to expose certain interior features.
Figure 7:
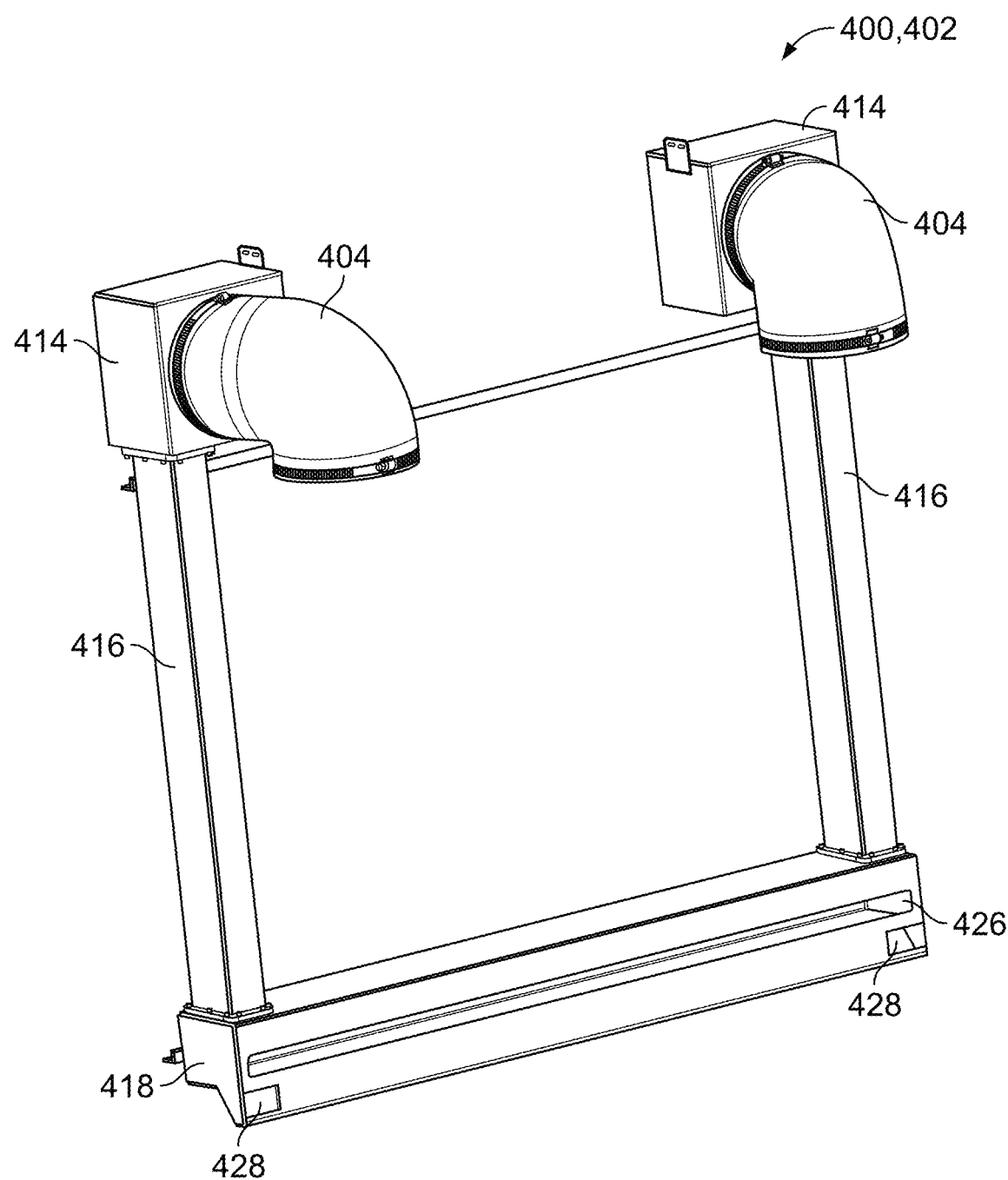
FIG. 7 is a front perspective view of the air duct frame of FIG. 6.
Figure 8:
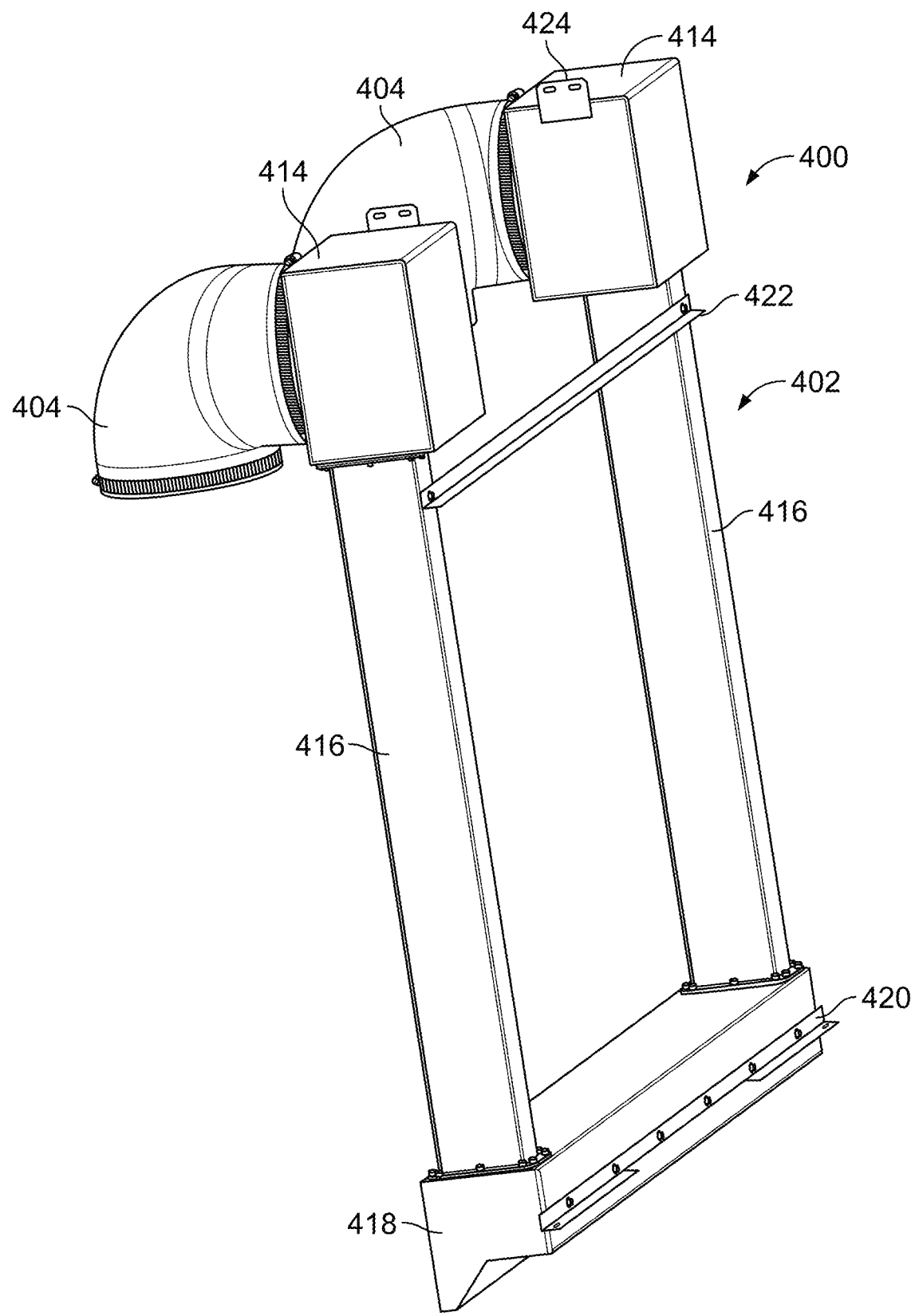
FIG. 8 is a rear perspective view of the air duct frame of FIG. 6.

Referring to FIGS. 1-3, the lower panel structure 204 includes a rear panel 208, two lateral panels 210, a front panel 212, and a lower panel 214 that together define an enclosure 216 that houses various components of the configurable workstation 100. The lower panel structure 204 further includes lower inner rails 218, upper inner rails 220, and support columns 222 that extend between the lower and upper inner rails 218, 220. The lateral panels 210 define lower outer rails 224 and upper outer rails 226. The lower outer rails 224 and the lower inner rails 218 together form feet 228 that support the weight of the configurable workstation 100. The upper outer rails 226 and the upper inner rails 220 together form upper support beams 230 that in part support the table 206, as will be discussed in more detail below.

The front panel 212 is equipped with multiple power outlets 232 at which any of the modules 300 or other accessory devices can be powered at the configurable workstation 100. The enclosure 216 houses several components that are accessible via a service panel 234. For example, the enclosure 216 houses a control module 236 that includes a printed circuit board (PCB) 238 on which the server computer 500 is implemented, a power supply 240 that powers the configurable workstation 100, and a power switch module 242 that manages distribution of the power.

Referring to FIGS. 1-4, the upper panel structure 202 includes a front panel 244 defining an opening 299 at which various modules 300 can be installed, a front cover 246, two lateral panels 248, a rear panel 250 defining an opening 297 that provides rear access to the opening 299, an upper panel 252, and a lower panel 254 that together define an enclosure 256 (e.g., a workstation hood) that houses various components of the configurable workstation 100. For example, the enclosure 256 is equipped with a pressure chamber 258 housing two oppositely located fans 260 that provide downward airflow within the frame 200, and a high-efficiency particulate air (HEPA) filter 262 located beneath the pressure chamber 258 for filtering the air. The front cover 246 is openable (e.g., pivotable at the upper panel 252) to switch out the HEPA filter 262 as needed.

The opening 299 of the front panel 244 has a rectangular shape to accommodate selected modules 300. The opening 299 typically has a width of about 1.0 m to about 2.0 m and a height of about 0.4 m to about 0.7 m (e.g., 1.08 m in the case of a 4-foot wide frame 200 or 1.67 m in the case of a 6-foot wide frame 200). The front panel 244 defines a row of vertically oriented, elongate openings 264 for airflow through the upper panel structure 202, as will be discussed in more detail below. The upper panel 252 defines a rectangular opening 295 through which air can flow along a selected airflow path at the frame 200.

Still referring to FIGS. 1-4, the rear panel 250 is equipped with a handle 266 for holding the rear panel 250 during assembly with or disassembly from the remaining components of the frame 200. The lower panel 254 is also equipped with lights that can illuminate the workspace 102. The upper panel structure 202 further includes lateral panels 268 that in part define the workspace 102 of the configurable workstation 100. The lateral panels 268 are transparent or translucent and therefore provide lateral viewing windows for the workspace 102. Example materials from which the lateral panels 268 may be made include glass, acrylic, or other types of transparent plastic. The lateral panels 248 define upper panel regions 270 that laterally close off the enclosure 256 and lower support beams 272 that in part provide support for the table 206.

FIG. 5 illustrates a schematic diagram of the control module 236 of the frame 200. The frame 200 is a stand-alone unit. That is, although the frame 200 has built-in structural and electronic support for the modules 300, the frame 200 can operate even without installation of any of the modules 300. Accordingly, the control module 236 of the frame 200 includes built-in hardware 293, built-in firmware 291, and a built-in user interface 289 to carry out its functionality. The control module 236 also includes the PCB 238 (e.g., a local mesh-network communication board), which implements the server computer 500.

Referring to FIGS. 4 and 6-8, the air duct system 400 can be removed from or installed to the frame 200 to change an air flow path at the configurable workstation 100. The air duct system 400 includes a duct frame 402, two air ducts 404 joined to the duct frame 402, a pressure chamber 406 housing a fan 408 for exhausting air out of the exhaust vent 412 and the upper opening 295 frame 200, a HEPA filter 410 for filtering the air flowing into the pressure chamber 406, and an exhaust vent 412 through which air flows out of the pressure chamber 406 and subsequently out of the frame 200 of the configurable workstation 100. The air ducts 404 are sealed to the duct frame 402 and are respectively located above and sealed to the fans 260 of the frame 200. The fans 260 are operated to rotate in a first rotational direction to flow air downward through the HEPA filter 262 and into the workspace 102 of the workstation. The fan 408 is operated to rotate in an opposite, second rotational direction to flow air upward through the HEPA filter 410, the pressure chamber 406, the exhaust vent 412, and out of the frame 200.

The duct frame 402 includes two compartments 414 that respectively interface with the air ducts 404, two vertical ducts 416 that extend from the compartments 414, a horizontal duct 418 that joins the two vertical ducts 416, a lower horizontal rear bracket 420 joined to the horizontal duct 418, and an upper horizontal rear bracket 422 that extends between the vertical ducts 416. Each compartment 414 is equipped with a vertical bracket 424. The air duct system 400 can be installed (e.g., attached) to the frame 200 with fasteners at the brackets 420, 422, 424. The horizontal duct 418 defines an elongate slot 426 that aligns with the row of openings 260 in the front panel 244 of the upper panel structure 202 to allow air to flow into duct frame 402. The horizontal duct 418 also defines two oppositely located rectangular openings 428 that align with duct components of the table 206 to allow air to flow into the duct frame 402, as will be discussed in more detail below.

The duct frame 402 typically has a total height of about 0.9 m to about 1.5 m, a total width of about 1.1 m to about 2.0 m, and a total depth of about 0.1 m to about 0.2 m. The duct frame 402 is a rigid structure that is typically made of one or more materials, such as steel, rubber, aluminum and thermal plastics. The air ducts 404 typically have an inner cross-sectional diameter of about 10 cm to about 25 cm. The air ducts 404 are flexible conduits that are typically made of one or more materials, such as aluminum, steel or plastics. The duct frame 402 and the air ducts 404 typically have a combined weight of about 20 lbs to about 45 lbs for easy handling.

Figure 9:
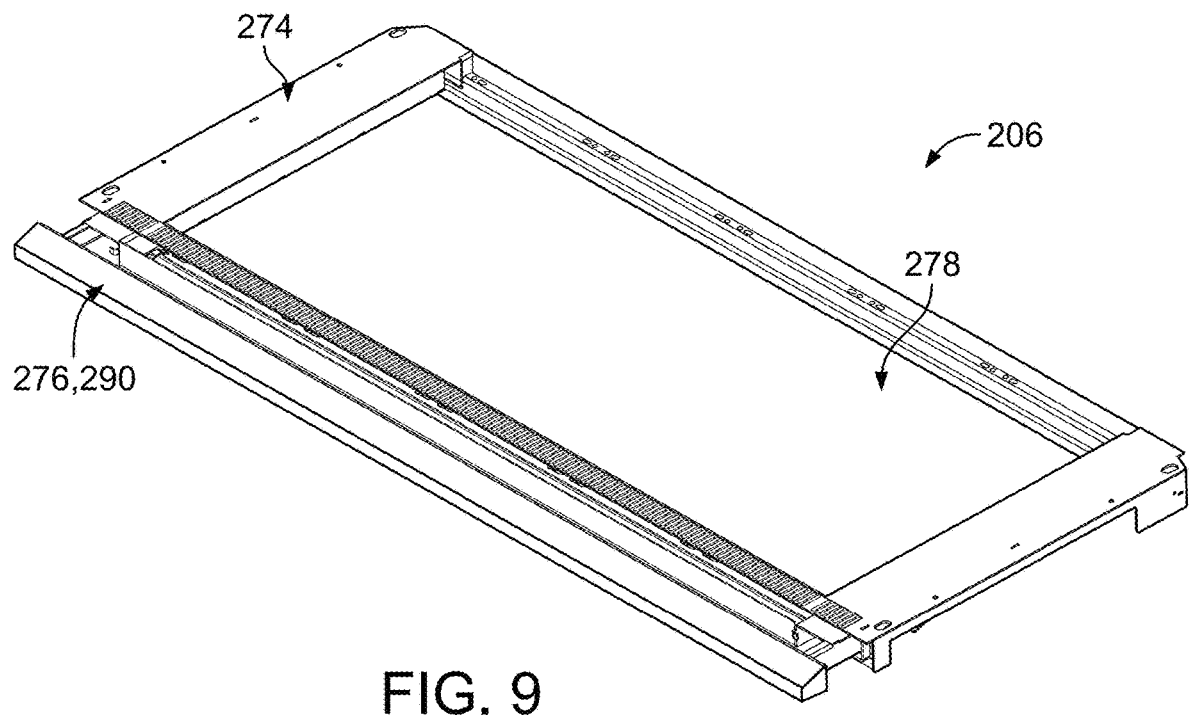
FIG. 9 is a perspective view of a table of the configurable workstation of FIG. 1.
Figure 10:
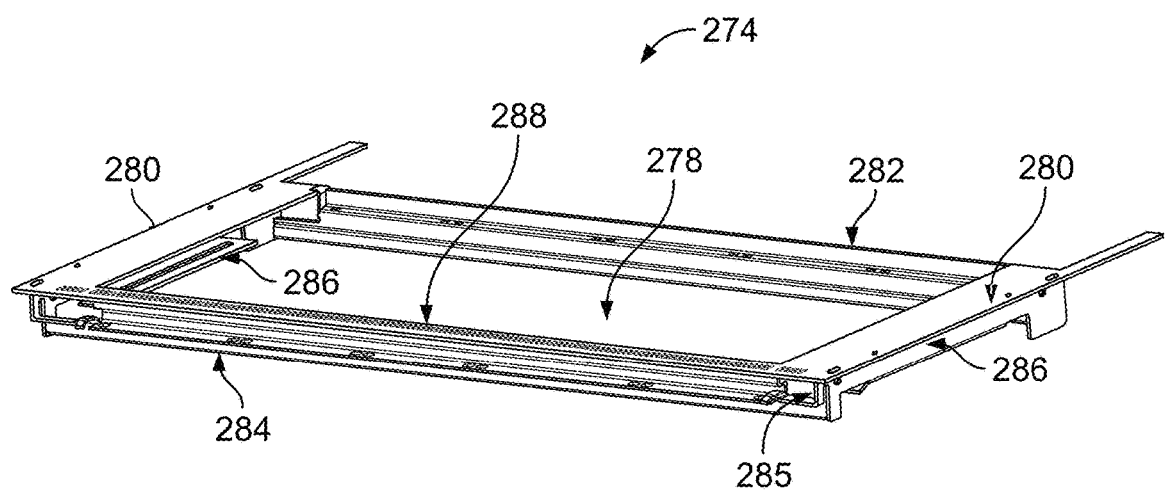
FIG. 10 is a perspective view of a platform of the table of FIG. 9.
Figure 11:
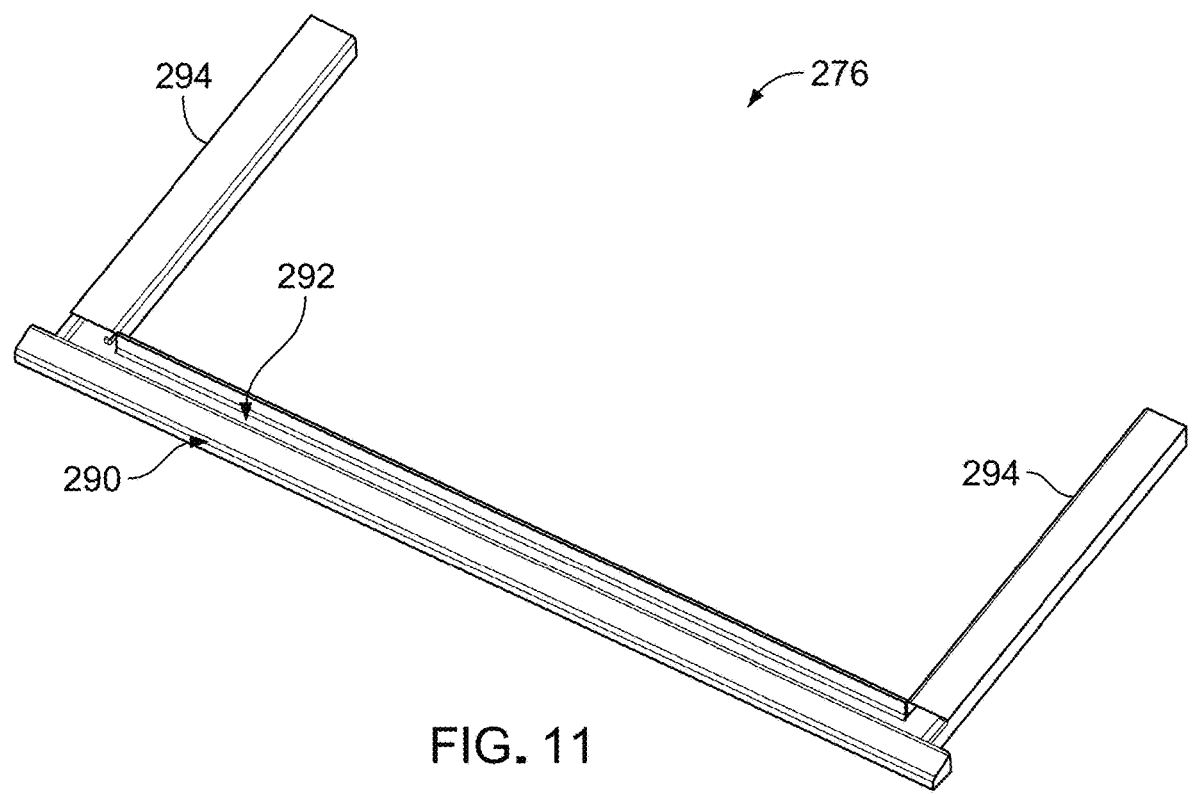
FIG. 11 is a perspective view of a slidable air duct of the table of FIG. 10.

Referring to FIGS. 9-11, the table 206 of the frame 200 includes a platform 274 and a slidable air duct 276 that can be withdrawn from and slid into the platform 274 like a drawer. The platform 274 defines an opening 278 at which various modules 300 can be installed to form a flat work surface within the workspace 102. The opening 278 has a rectangular shape to accommodate selected modules 300. The opening 278 typically has a width of about 1.0 m to about 2.0 m (e.g., 1.05 m in the case of a 4-foot wide frame 200 or 1.7 m in the case of a 6-foot wide frame 200) and a depth of about 0.4 m to about 0.6 m.

The platform 274 also defines two lateral sections 280 by which the table 206 is attached to the lower support beams 272 of the upper panel structure 202 and the upper support beams 230 of the lower panel structure 204. The lateral sections 280 also extend rearwardly along the horizontal duct 418 of the air duct frame 400. The platform 274 further defines a rear bracket 282 and a front bracket 284 by which the modules 300 can be attached to the table 206 and lateral brackets 286 that provide support for the slidable air duct 276. The rear and front brackets 282, 284 define rectangular openings 285 through which components of the slidable air duct 276 pass to communicate with the air duct system 400. The platform 274 also defines a frontal row of elongate openings 288 through which air in the workspace 102 can flow into the slidable air duct 276 and subsequently into the air duct system 400.

Still referring to FIGS. 9-11, the slidable air duct 276 defines an elongate handle 290 by which the slidable air duct 276 can be pulled from the table 206 and by which the slidable air duct 276 can be pushed (e.g., slid) forward along the lateral brackets 286 of the table 206. The slidable air duct 276 further defines an open front channel 292 that extends along the handle 290 and two lateral conduits 294 that extend rearwardly from the front channel 292. A filter may be positioned within the slidable air duct 276 at a front end of each lateral conduit 294 to prevent any large objects from entering the lateral conduits 294.

Figure 12:
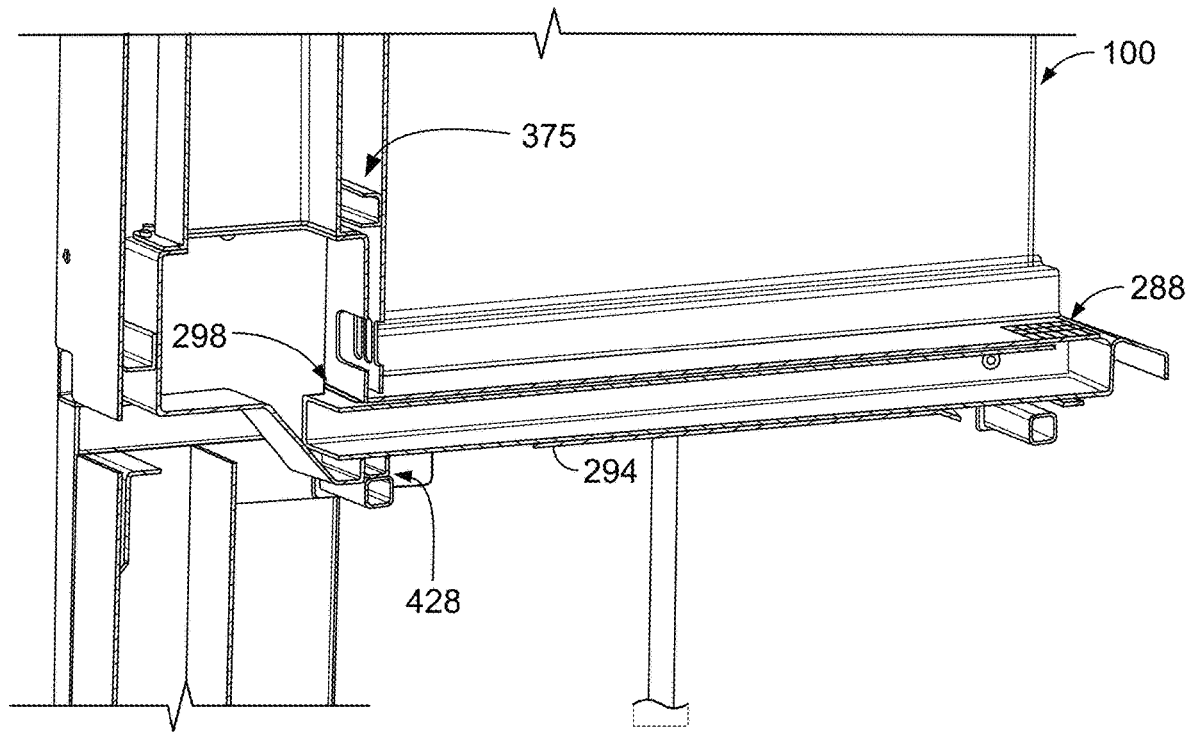
FIG. 12 is an enlarged perspective view of an interface between the slidable air duct of FIG. 11 and the air duct frame of FIG. 6.
Figure 13:
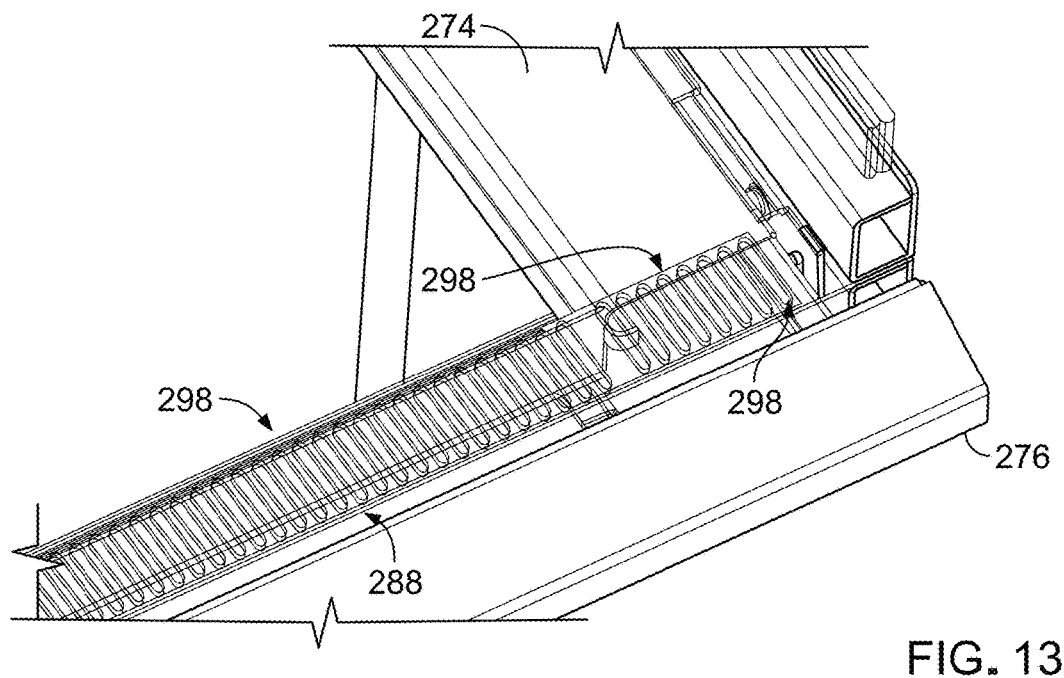
FIG. 13 is an enlarged perspective view of a frontal portion of the table of FIG. 6.

Referring to FIGS. 12 and 13, when the slidable air duct 276 is positioned at a rearward most position (e.g., pushed against the platform 274), the front channel 292 is positioned underneath the openings 288 of the platform 274, and rear ends 296 of the lateral conduits 294 are positioned within the rectangular openings 428 of the duct frame 402. One or more seals 298 may be installed along the slidable air duct 276 to seal the slidable air duct 276 to the rectangular openings 428 and to the platform 274. The slidable air duct 276 may be pulled forward from the platform 274 so that the front channel 292 and the lateral conduits 294 can be cleaned and sanitized of any fluids or other objects that have fallen into the slidable air duct 276. The slidable air duct 276 may remain in partial contact with the platform 274 or may be removed completely from the platform 274.

The frame 200 is a rigid structure that typically has a total height of about 1.8 m to about 3.0 m, a total width of about 1.0 m to about 2.0 m, and a total depth of about 0.5 m to about 1.0 m. The various components of the frame 200 (e.g., including the upper panel structure 202, the lower panel structure 204, and the table 206) are typically made of one or more materials that can chemically withstand various laboratory cleaning substances. Example materials from which the frame 200 may be made include steel, aluminum, glass, and plastic. The frame 200 (e.g., excluding the modules 300 and the air duct system 400) typically has a weight of about 350 lbs to about 1200 lbs.

Figure 14:
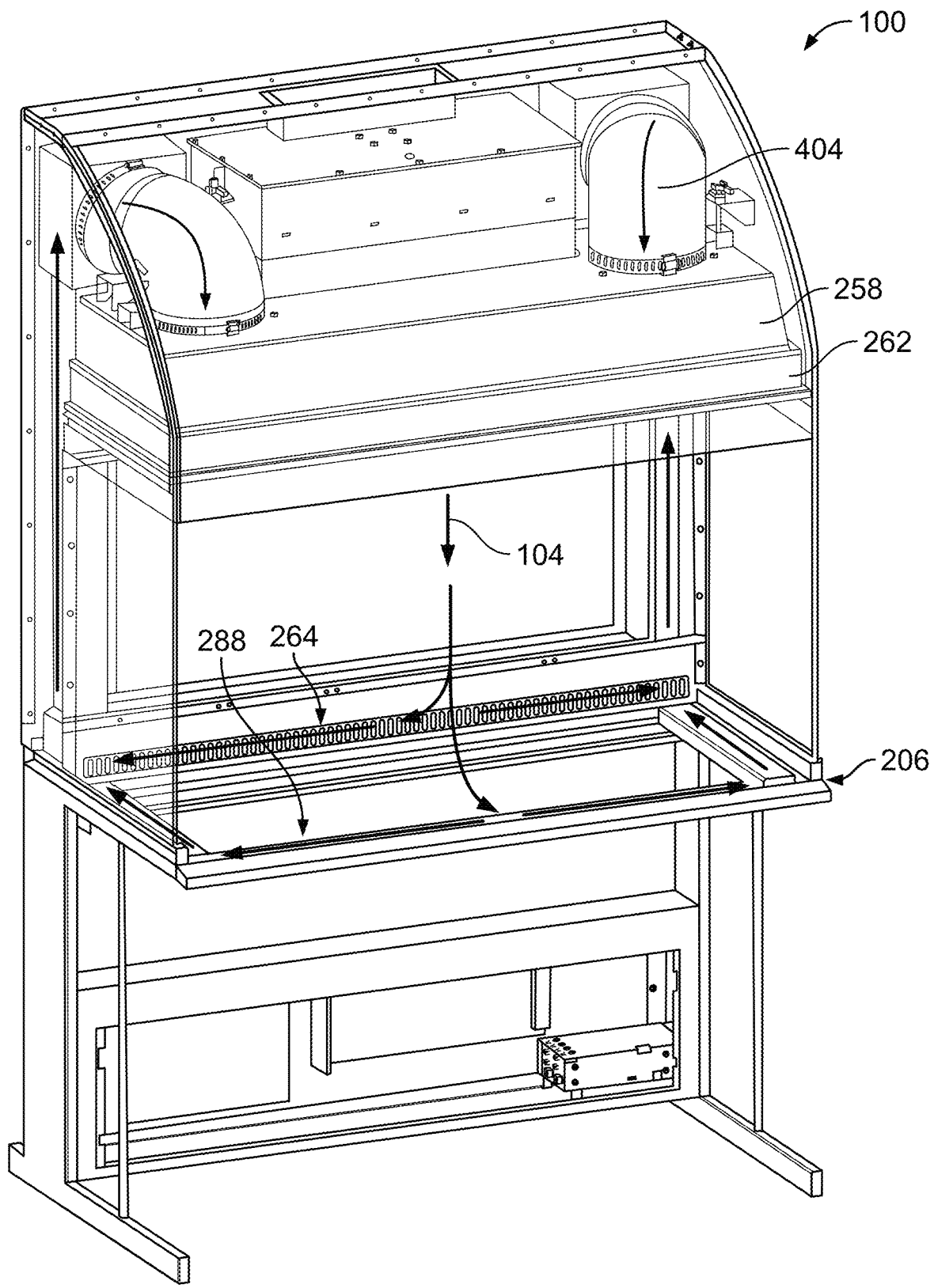
FIG. 14 illustrates an airflow path at the configurable workstation of FIG. 1 embodied as a Class II biosafety cabinet.

Referring to FIG. 14, the workstation 100 is embodied as a Class II biosafety cabinet (e.g., with or without any of the illustrated modules 300), such that an airflow path 104 at the workstation 100 is designed to protect personnel working at the workstation 100, an environment at which the workstation 100 is located, and any specimens (e.g., product) handled in the workspace 102 from contaminants or other particulates present near the workstation 100. In order to meet certain requirements of a Class II biosafety cabinet, the fans 260 within the pressure chamber 258 recirculate air within the workspace 102 along the airflow path 104 by flowing the air beneath the table 206 and back through the HEPA filter 262 before the air reenters the workspace 102.

For example, air within the workspace 102 is circulated in a downward direction and then rearwardly into the openings 264 of the upper panel structure 202, where the air passes through the elongate slot 426 of the horizontal duct 418 to enter the duct frame 402. Air within the workspace 102 is also circulated forwardly into the openings 288 of the platform 274, where the air passes into the front channel 292 of the slidable aid duct 276, flows further into the lateral conduits 294, and then flows through the rectangular openings 428 of the horizontal duct 418 to enter the duct frame 402. Air within the horizontal duct 418 is circulated upward through the duct frame 402, drawn into the air ducts 404, and driven downward by the fans 260 through the HEPA filter 262 to remove any harmful particles or contaminants before reentering the workspace 102. Thus, the fans 260 circulate air along the airflow path 104 through the workspace 102, the slidable air duct 276, and the duct frame 402 to meet certain Class II requirements. By flowing the air laterally towards sides of the frame 200 and rearwardly through the front panel 244, the air avoids contact with other components of the configurable workstation 100 which may otherwise increase the likelihood of air contamination, as is the case for conventional biosafety cabinets.

The slidable air duct 276 of the table 206 and the air duct system 400 are designed such that the airflow path 104 is unaffected by the combination of modules 300 installed at the frame 200. Independence of the airflow path 104 from the modules 300 advantageously permits factory testing of the airflow path 104 prior to shipment of the configurable workstation 100 to a customer site.

Figure 15:
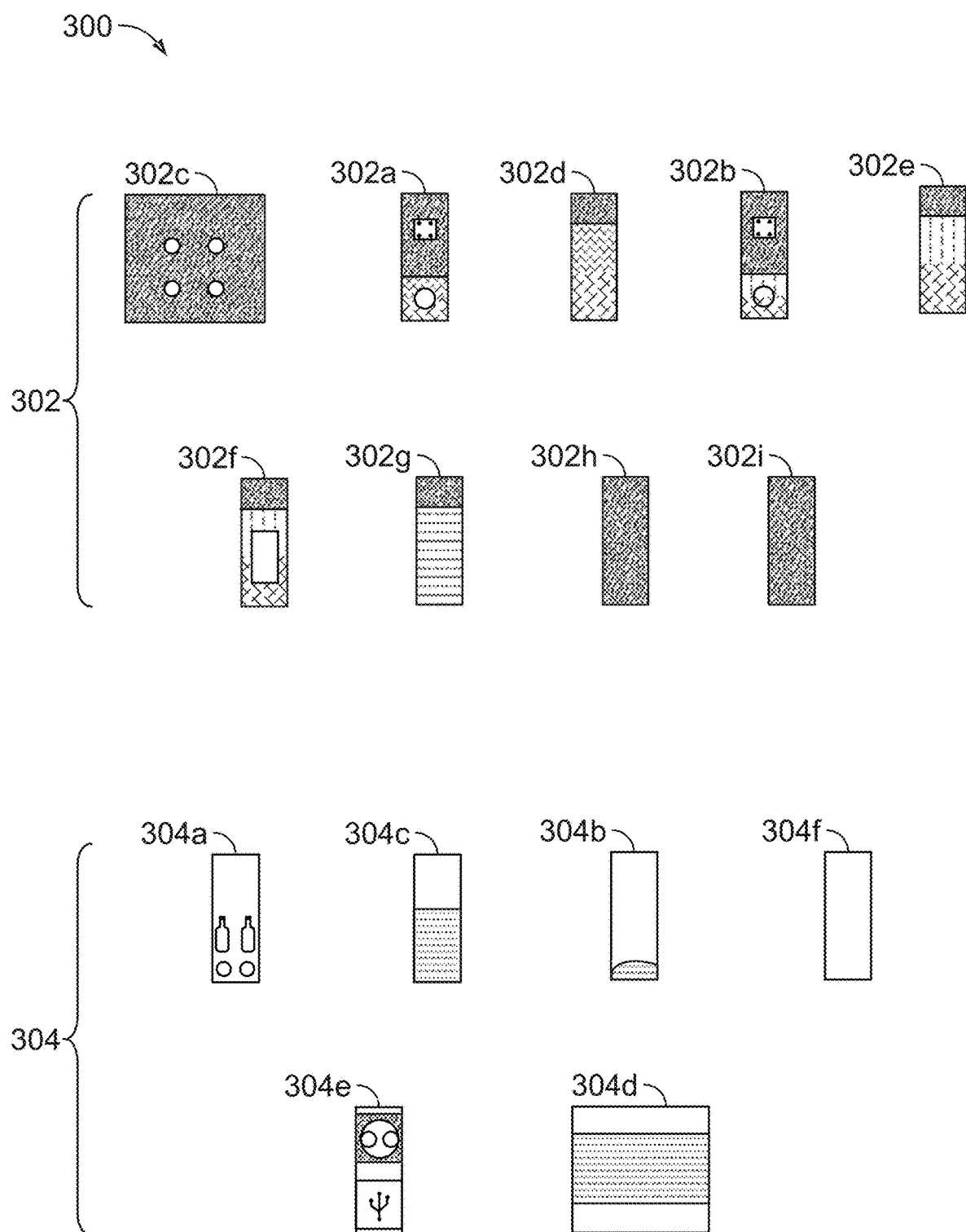
FIG. 15 is a schematic illustration of modules of the configurable workstation of FIG. 1.

Referring to FIGS. 15, the modules 300 are standalone units and include functional modules and non-functional blanks that can be selectively installed to the table 206 and the front panel 244 of the frame 200 to customize a functional profile of the workstation 100. For example, by selectively installing desired modules 300, the functional profile may be customized to provide capabilities required to carry out certain experimental procedures, to meet certain requirements of a laboratory at which the workstation 100 is located, or to identify specimens in a certain manner. The functional modules are operable to perform clinical functions and are therefore classified as medical devices that are subject to regulatory review. The non-functional blanks cannot perform any clinical functions and are therefore not subject to regulatory review.

The modules 300 include table-top modules 302 that are designed to lay horizontally and to be installed at the table 206. Depending on a width of the frame 200, a total number of 5 to 10 modules 302 may be installed to the table 206 at the same time. Once the modules 302 are positioned at the table 206, the modules 302 need to be flush with each other so that certain specimens, tools, equipment, and procedures are not damaged, obstructed, or otherwise flawed due to unexpected variability in height of the work surface across the table 206. Additionally, gaps between the modules 302 should be minimized to ensure smooth surface transitions between adjacent modules 302. Gaps between the modules 302 should also be sealed to prevent any materials from leaking into the gaps and subsequently resulting in bacterial growth that will be detrimental to biomedical procedures performed in the workspace 102.

The modules 302 include modules 302a-302i. The module 302a is a heating plate with microscope mounting holes and a heated transparent glass. The module 302b is a heating plate with microscope mounting holes, a heated transparent glass, and built-in RFID capabilities for detecting RFID tags that identify a specimen for patient sample tracking. The module 302c is an anti-vibration table that provides a platform template with four holes at which an anti-vibration table can be installed at the table 206. The module 302d is a heating plate that can achieve a user-set temperature, and the module 302e is a heating plate with RFID capabilities. The module 302f is an incubator that can provide one or more features including pH monitoring, programmable heat and gas cycles, controlled heating, and $CO_2$, $O_2$, and $N_2$ gas mixtures suitable for long-term embryo incubation and development. The module 302g is a cooling unit that can cool or vitrify a specimen. The modules 302a-302g are medical devices that are subject to regulatory review.

The module 302h is a blank that can fill in part of the opening 278 at the table 206 to provide a complete table-top surface, and the module 302i is a blank with RFID capabilities that can fill in part of the opening 278 at the table 206 to provide a complete table-top surface. The modules 302h, 302i are non-medical devices and are therefore not subject to regulatory review. Any of the modules 302a-302i may additionally provide a light source for the workspace 102.

The modules 300 also include wall modules 304 that are designed to be oriented vertically and to be installed at the front panel 244 of the upper panel structure 202. Depending on a width of the frame 200, a total number of 5 to 10 modules 304 may be installed to the front panel 244 at the same time. The modules 304 include modules 304a-304f. The module 304a is a humidifier that can heat containers of water and flow gas through the water to provide humidified gas for an IVF procedure or other procedures carried out in the workspace 102. The module 304a is a medical device that is subject to regulatory review. The module 304b is an ICSI arch that provides a concave cavity to allow room for micromanipulators and inverted microscopes to be installed in the workspace 102. The module 304c is a wall tunnel that provides a passageway for a user to pass items (e.g., equipment, specimens, and other items) through the front and rear panels 244, 250 of the upper panel structure 202. The module 304d is a monitor (e.g., a computer monitor or other display, such as a 27 inch or 32 inch monitor).

The module 304e is an outlet panel that may provide one or more universal power outlets or USB outlets. The module 304f is a blank that can fill in part of the opening 299 at the front panel 244 of the upper panel structure 202 to provide a complete wall surface. The modules 304b-304f are non-medical devices and are therefore not subject to regulatory review. Any of the modules 304a-304f may additionally provide a light source for the workspace 102.

Figure 16:
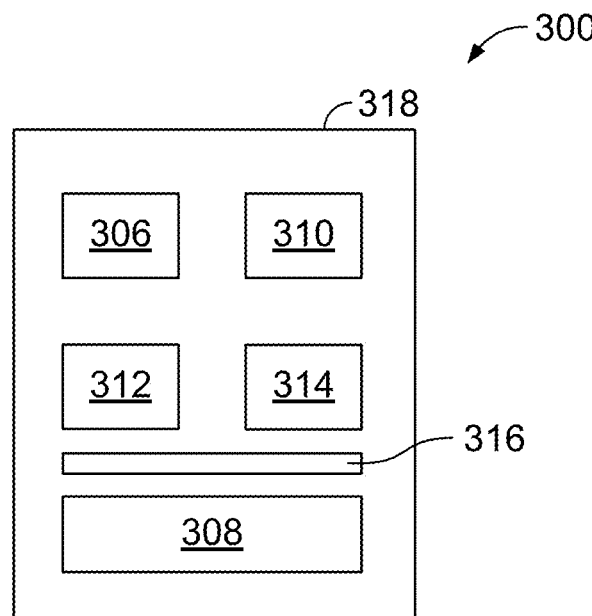
FIG. 16 is a schematic illustration of certain modules of FIG. 15.

FIG. 16 illustrates a schematic diagram of a module 300 that may represent any of the above-described modules 302a-302i, 304a-304f. The modules 300 are self-contained units. That is, as long as power is supplied to a module 300 at a built-in power port 306, the module 300 can operate even without installation to the frame 200 and can perform their intended functionalities without connection to the web application implemented on the server computer 500. Accordingly, each functional module 300 includes built-in equipment 308 for carrying out its dedicated laboratory function (e.g., such as any of the functions discussed above with respect to FIG. 15), built-in hardware 310, built-in firmware 312, and a built-in user interface 314 to carry out its functionality. Each module 300 also has a built-in local mesh network communication board 316 to allow for wireless communication to the server computer 500 to receive user inputs. The modules 300 may have alarms and controls for basic functions (e.g., a set point edit), while other functions (e.g., calibration, logging, and other functions) may be performed at an application running on the server computer 500, as will be discussed in more detail below.

Figure 17:
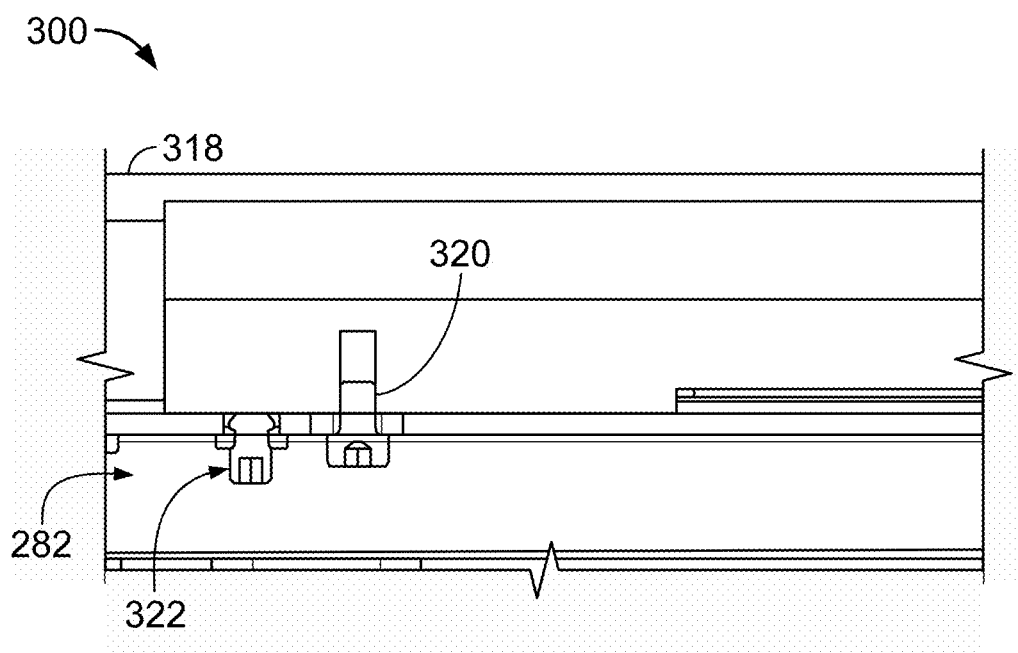
FIG. 17 is a cross-sectional schematic view of an interface between a module of FIG. 15 and the table of FIG. 9 with a push and pull fasteners.
Figure 18:
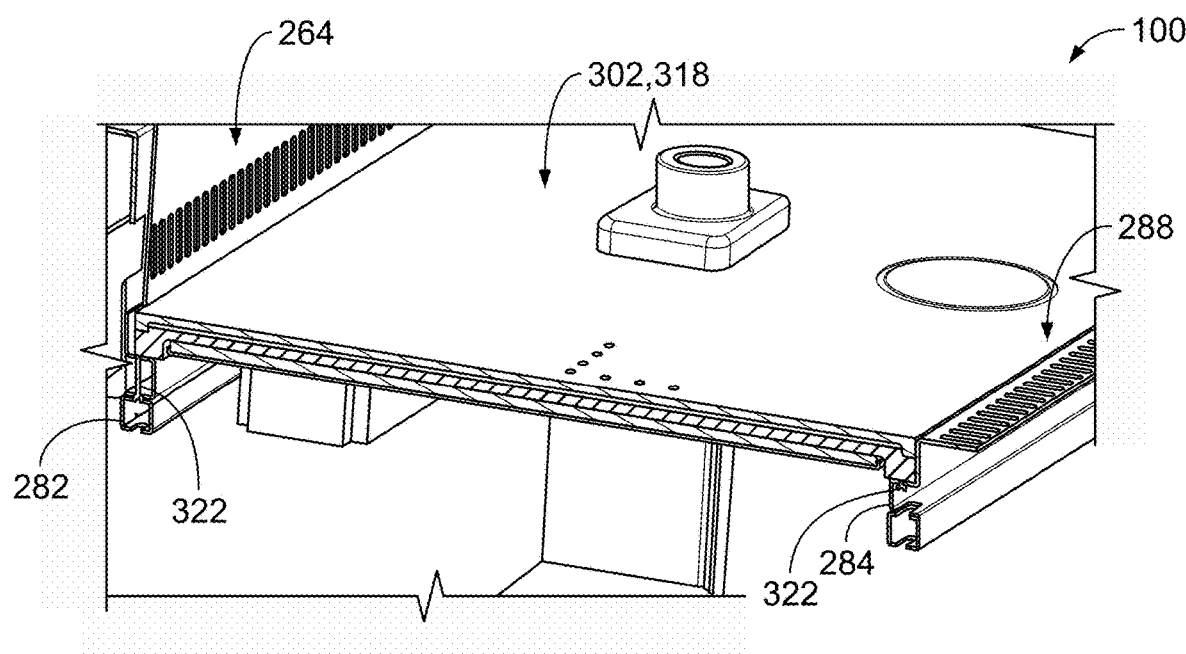
FIG. 18 is a cross-sectional view of an interface between a module of FIG. 15 and the table of FIG. 9 with the push fastener of FIG. 17.
Figure 19:
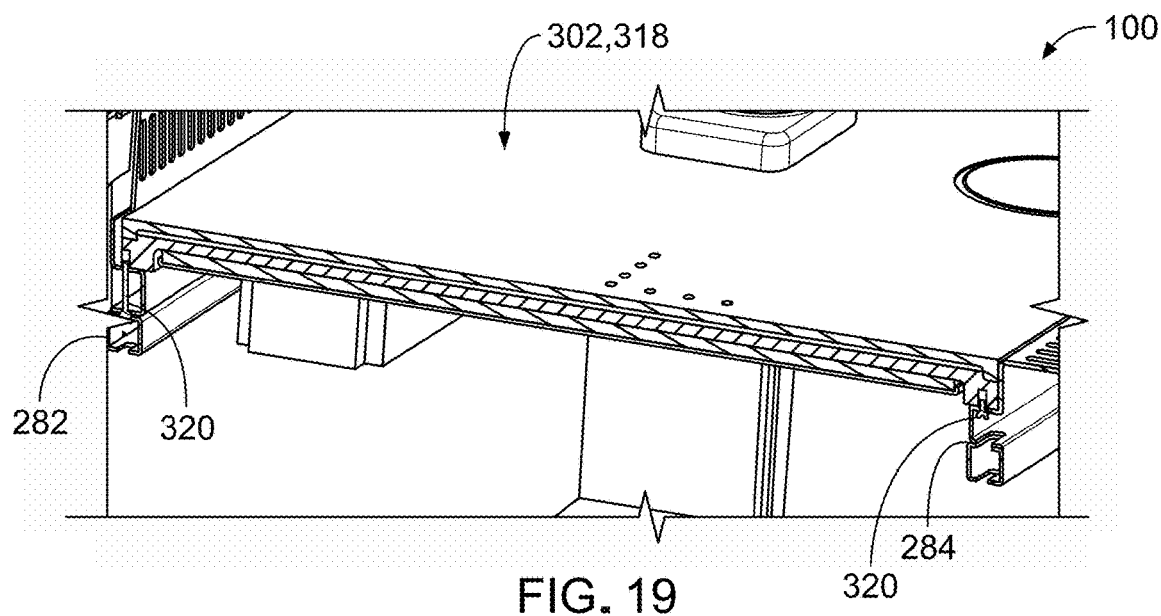
FIG. 19 is a cross-sectional view of an interface between a module of FIG. 15 and the table of FIG. 9 with the pull fastener of FIG. 17.

Referring to FIGS. 17-19, each table-top module 302 includes one or more generally flat components that form a housing 318. The module 302 is placed atop the rear bracket 282 and the front bracket 284 of the table 206 within the opening 278 of the platform 274 for installation to the table 206. The module 302 is attached to the brackets 282, 284 with one or more fasteners 320 (e.g., socket screws or the like) that pull the module 302 downward towards the table 206 to lock the module 302 in position. The module 302 is also engaged with the brackets 282, 284 with one or more fasteners 322 (e.g., set screws or the like) that push the module 302 upward for level adjustment of the module 302 with the platform 274 of the table 206 and with any adjacent module 302 to provide a flat work surface across the table 206.

Figure 20:
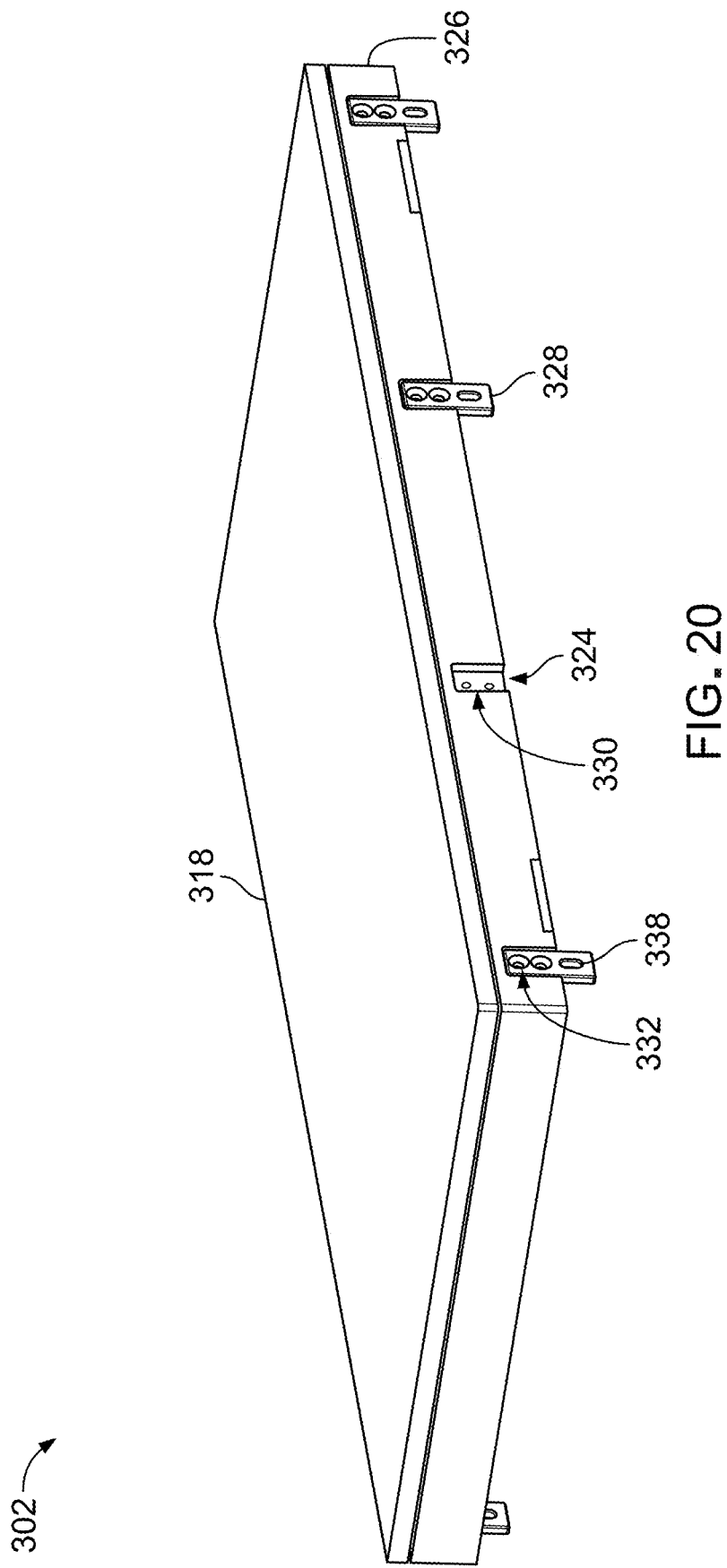
FIG. 20 is a perspective view of a module of FIG. 15 equipped with adjustment blocks.
Figure 21:
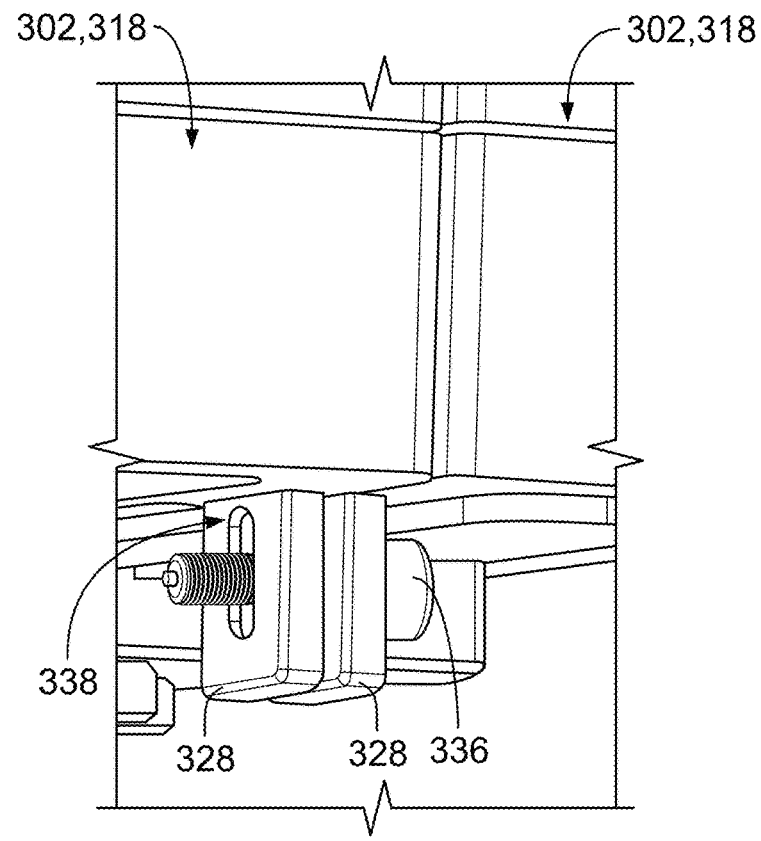
FIG. 21 is an enlarged perspective view of two modules of FIG. 15 connected to each other via two adjustment blocks of FIG. 20.

Referring to FIGS. 20 and 21, the housing 318 defines multiple recesses 324 along lateral edges 326 that are sized to accommodate an attachment block 328 by which the module 302 can be secured laterally to an adjacent module 302. The recesses 324 and the attachment blocks 328 respectively define holes 330, 332 through which a fastener can be passed to secure the attachment block 328 to the housing 318 of the module 302. A fastener 336 can be passed through vertical slots 338 of respective adjacent adjustment blocks 328 attached to adjacent modules 302 to secure the modules 302 to each other laterally (e.g., to pull the adjacent modules 302 towards each other). A length of the vertical slot 338 allows for flexible vertical positioning of the adjacent adjustment blocks 328 (e.g., being attached to the modules 302) as desired to level the modules 302 with respect to each other.

Figure 22:
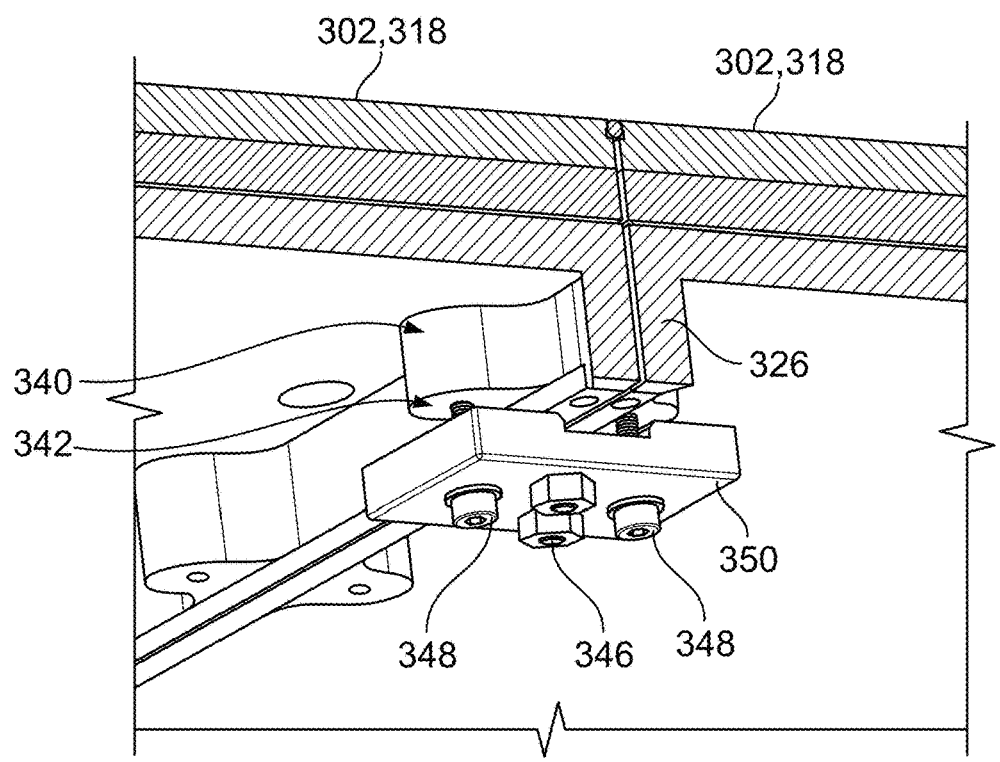
FIG. 22 is a bottom perspective view of an interface of two modules of FIG. 15 connected by an adjustment block.
Figure 23:
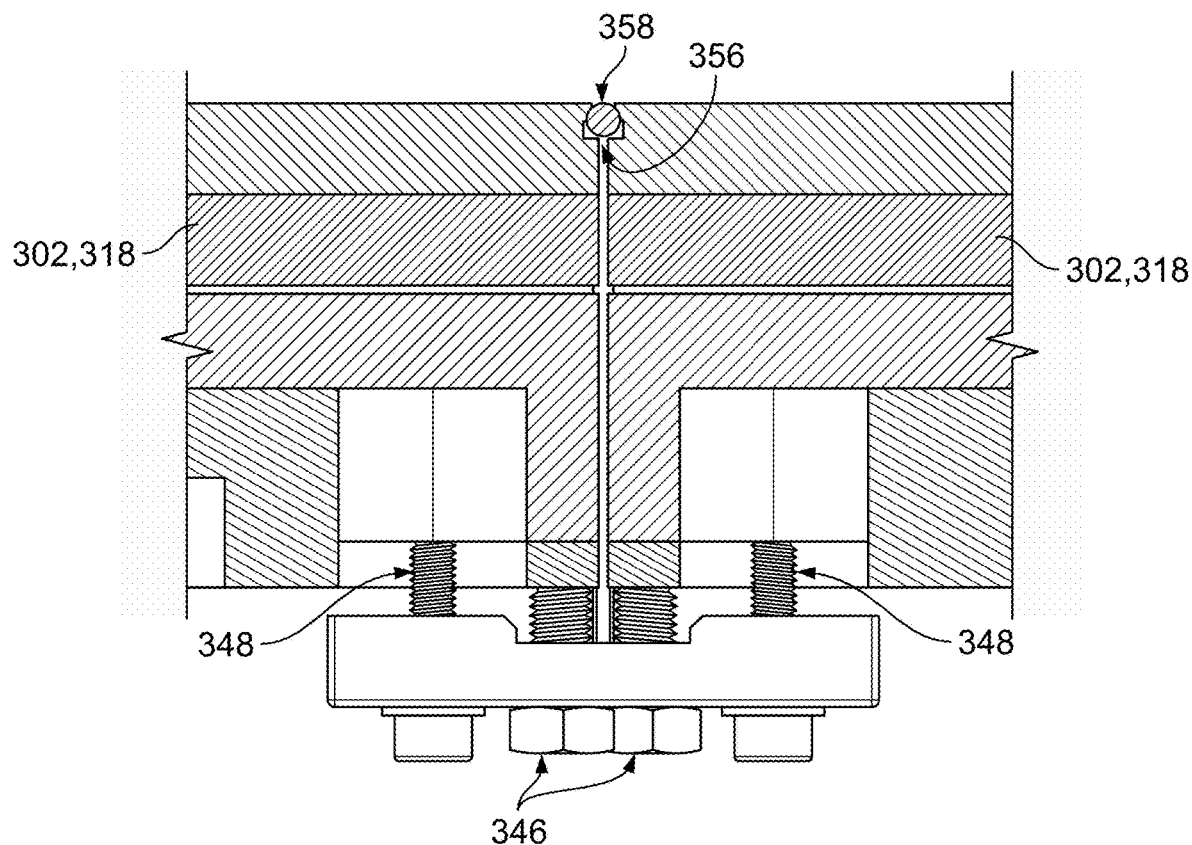
FIG. 23 is a side view of the interface of FIG. 22.
Figure 24:
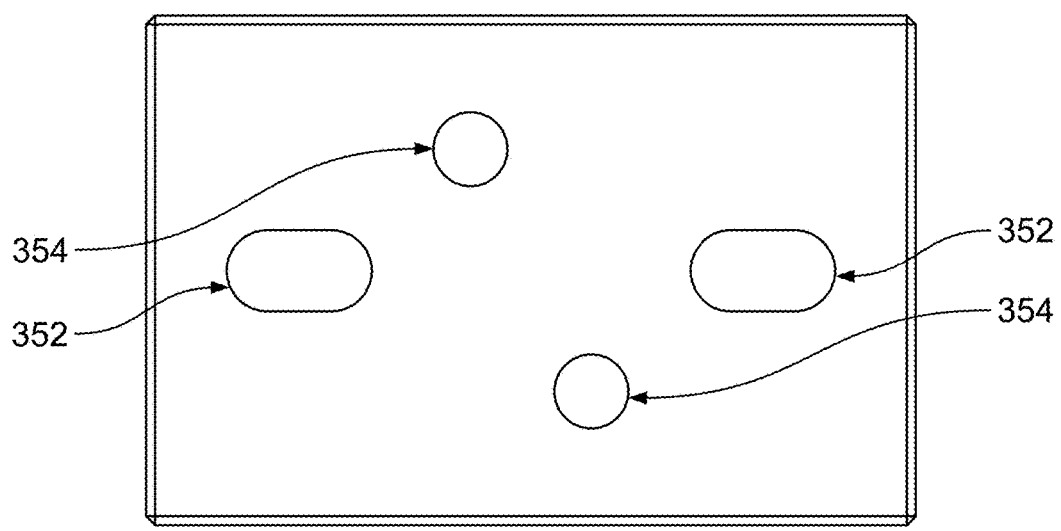
FIG. 24 is a top view of the adjustment block of FIG. 22.

Referring to FIGS. 22-24, the housing 318 of the module 302 also defines protrusions 340 directed inwardly from the lateral edges 326. Each protrusion 340 defines a central opening 342 that accommodates a screw fasteners 346 by which the module 302 can be laterally secured to and leveled with respect to an adjacent module 302 alternatively or additionally using an adjustment block 350. Optional positions of the adjustment block 350 do not interfere with optional positions of the adjustment block 328. The adjustment block 350 has a pattern defined by holes 352 and slots 354. A length of the slots 354 allows for flexible lateral positioning of fasteners 348 within the slots 354 for desired lateral positioning of the module 302 with respect to an adjacent module 302. The fasteners 348 (e.g., socket screws or the like) are used to pull the module 302 towards the adjustment block 350 to lock a position of the adjustment block 350 in place against the adjacent modules 302, while the fasteners 346 (e.g., set screws of the like) are used to push the modules 302 upward as desired to level modules 302 with respect to each other.

Once secured in position, adjacent modules 302 define an intermediate groove 356 along the lateral edges 326. Each module 302 is provided with a gasket 358 that may be pressed into the groove 356 to prevent any spills that occur atop the table 206 from flowing downward in between the modules 302.

Figure 25:
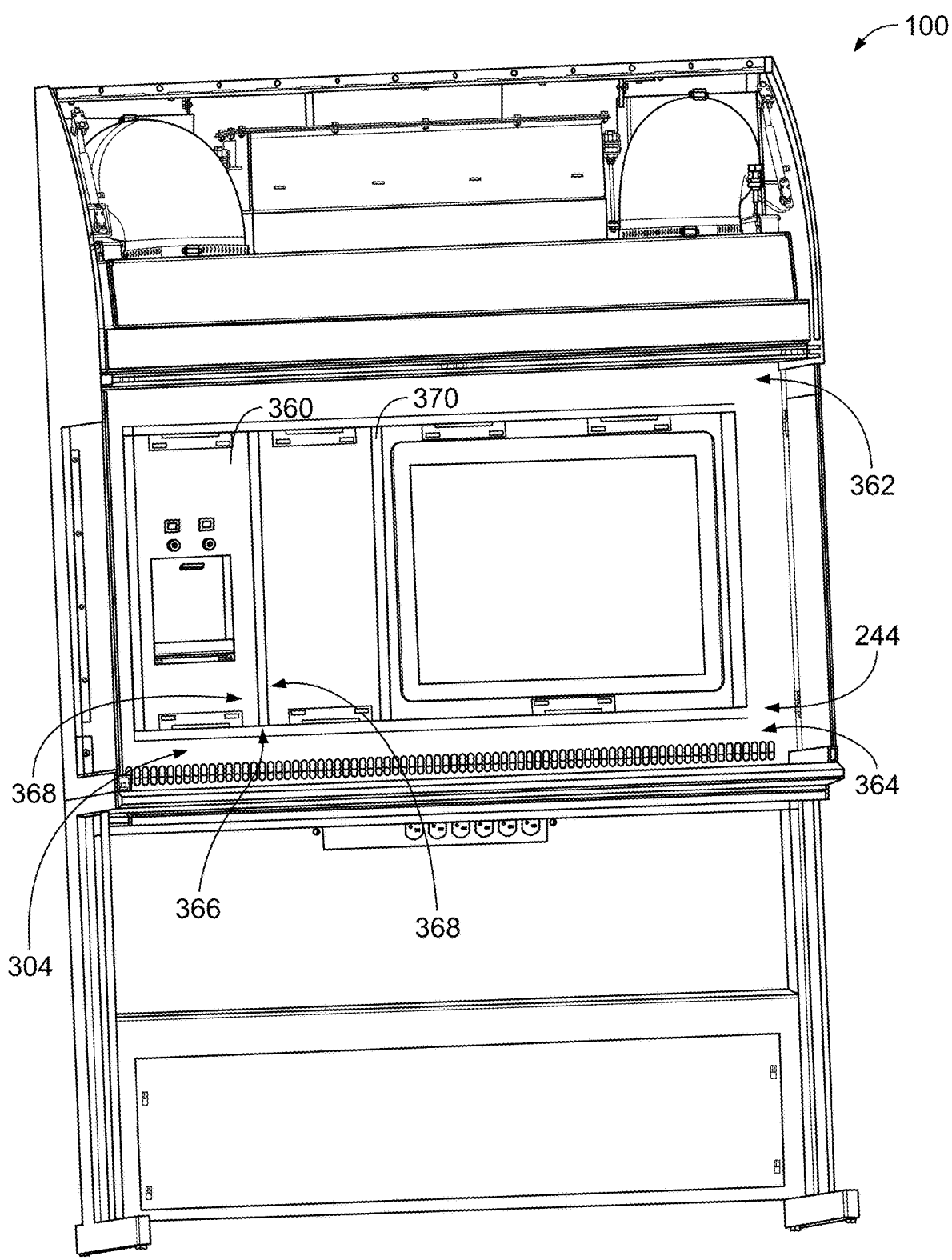
FIG. 25 is a front perspective view of wall modules of FIG. 15 installed to a front panel of the configurable workstation of FIG. 1.

Referring to FIGS. 25 and 26, each wall module 304 includes an installation panel 360 that is attachable via fasteners (e.g., screw fasteners or other fasteners) along upper and lower edges 362, 364 to the front panel 244 of upper panel structure 202 of the frame 200. Various equipment features 308 may be assembled with the installation panel 360, depending on a functionality of the module 304. Once secured in position, adjacent modules 304 define an intermediate groove 366 along the lateral edges 368. Each module 304 is provided with a gasket 370 that may be pressed into the groove 366 to prevent any undesired airflow between the modules 304. The gasket 370 includes an insertion piece 372 that is pressed into the groove 366 and a flange 374 that covers the groove 366 to provides a seamless feel and appearance across the front panel 244.

Referring again to FIGS. 2 and 4, the installation panel 360 is also equipped with one or more spring-like mechanisms 287 that secure the selected wall modules 304 in place in the opening 299 of the front panel 244. The spring-like mechanisms 287 are designed to latch onto and push on a rear wall rail 375 (refer to FIG. 12). The spring-like mechanisms 287 also provide support surfaces on which the modules 304 can rest against the rear wall rail 375 such that the spring-like mechanisms 287 support the weight of the modules 304. The combined features of, latching, pushing and support ensure the modules 304 are substantially flush against the opening 299 during operation.

In some embodiments of the modules 302, the housing 318 has a total length of about 0.6 m to about 0.7 m (e.g., about 0.64 m), a total width in a range of about 0.4 m to about 2.0 m (e.g., about 0.43 m), and a total thickness of about 0.025 m to about 0.7 m (e.g., about 0.03 m). Fasteners 320, 322 are typically secured to a housing 318 of a module 302 at a distance of about 0 cm to about 0.1 cm from a lateral edge 326 of the module 302. The adjustment block 328 typically has a length of about 1.0 cm to about 10.0 cm, a width of about 0.5 cm to about 3.0 cm, and a thickness of about 0.1 cm to about 2.0 cm. The adjustment block 350 typically has a length of about 0.5 cm to about 10.0 cm, a width of about 0.5 cm to about 4.0 cm, and a thickness of about 0.1 cm to about 3.0 cm. In some embodiments of the modules 304, the installation plate 360 has a length of about 40.0 cm to about 70.0 cm, a width in a range of about 18.0 cm to about 200.0 cm, and a thickness of about 0.1 cm to about 1.0 cm.

The housing 318, the installation plate 360, and the adjustment blocks 328, 350 are rigid structures that are typically made of one or more materials that can chemically withstand various laboratory cleaning substances. Example materials from which these components may be made include steel, aluminum, and thermal plastics. Each tabletop module 302 typically weighs between about 10 lbs and about 60 lbs, while each wall module 304 typically weighs between about 2 lbs and about 50 lbs. The gaskets 358, 370 are also designed to withstand various laboratory cleaning substances and are therefore typically made of one or more materials, such as rubber, silicone, Buna-N-Nitrile, and soft plastics.

Referring to FIG. 27, the server computer 500 provides a central user interface between a user (e.g., an embryologist or another clinician) and the frame 200 and the modules 300 for monitoring statuses of the frame 200 and the modules 300 and for inputting parameters (e.g., set points) that govern operations of the frame 200 and the modules 300. The server computer 500 hosts a web application that can be accessed via a local Ethernet line or via WiFi connection to allow the user to control all functions of the frame 200 and the modules 300 from a single location. The web application, itself, does not perform any clinical functions. Rather, the web application conveys and communicates information gathered and handled by the frame 200, the modules 300, and users. The server computer 500 can establish connections to transfer data from the Ethernet line or WiFi connection to a local mesh network to which the modules 300 and the frame 200 are connected.

For example, the configurable workstation 100 operates on a network communication architecture 502 for the electronically-enabled devices 504 (e.g., the frame 200 and the modules 300) of the configurable workstation 100. The network communication architecture 502 alleviates privacy and performance concerns related to handling and storing medical data by supporting the devices 504 (e.g., devices 504a-504e) on a local network to reduce a chance of unauthorized access to the devices 504 and data stored on or transferred by the devices 504. The network communication architecture 502 is also flexible to handle a variable number of devices 504 without prior customization at a factory.

The architecture 502 includes three communication layers 506, 508, and 510. The layer 506 includes a local mesh network 512 (e.g., a private network) that provides communication connections between the devices 504. The layer 508 (e.g., a private network) provides connections between the devices 504 of layer 506 and the server computer 500. The layer 510 provides connections to remote servers or databases, such as a remote server on a cloud 514. The devices 504 and the server computer 500 provided by the workstation 100 are located in a laboratory of a medical facility (e.g., a hospital or a medical clinic), while the cloud 514 is located outside of the medical facility.

None of the devices 504 in the layer 506 is in direct communication with the cloud 514. Rather, all communications between the local mesh network 512 and the outside world are handled through the server computer 500. The server computer 500 verifies security criteria of data before allowing the data to be transferred to or from the outside world to the devices 506 in the local mesh network 512. This communication configuration protects security of data on the devices 504 and prevents unauthorized access from the outside world to the devices 504. In addition, even if connection between the server computer 500 and the cloud 514 is lost, the devices 504 can continue operating and communicating with each other through the local mesh network 512 and with the server computer 500.

The devices 504 (e.g., the devices 504*a*-504*e*) can communicate with each other through the local mesh network 512 in a wireless or wired manner. Additionally, each of the devices 504 can communicate with the server computer 500 independently of the other devices 504 such that if one device 504 malfunctions, the operation (e.g., functionalities and communications) of the remaining devices 504 will not be hindered or affected. In this manner, the network communication architecture 502 ensures device independence. Not only is independence of the devices 504 important for customer needs and technically robust, but such independence advantageously allows independent handling (e.g., access and control) of devices 504 in distinct regulatory classes. Accordingly, a regulatory approval status for one device 504 will not affect a regulatory approval status of another device 504.

Since a device 504 may have a processor with limited functionalities, the device 504 may need to communicate its data to a more powerful processor to further analyze, transform, or present the data to a user or to another computing device. For example, a device 504*a* may communicate its data to the server computer 500. The server computer 500 receives the data from the device 504*a*, analyzes the data, and provides an output based on the analysis. In some implementations, the output may be displayed to a user (e.g., at a module 304*d* installed to the front panel 244 of the frame 200). The user can also interact with the application running on the server computer 500 to send data to individual devices 504 via the local mesh network 512.

In some implementations, the output may be communicated to other computing devices. For example, the server computer 500 may send the output to a device 504*b* on the local mesh network 512, to a client device 516 (e.g., a tablet, a mobile phone, a laptop computer, or a desktop computer, etc.) to a local database or a local server 518, or to a remote server on the cloud 514. The server computer 500 can communicate with the local server 518 or with the client device 516 through a local area network (LAN) of the medical facility. The local server 518 can be located in the same medical facility as where the server computer 500 (e.g., on the workstation 100) is located. Applications with the required credentials can access the server computer 500 to access data from the devices 504 such that the medical facility need only provision the server computer 500 on its LAN and not each device 504 individually. The server computer 500 can communicate with the cloud 514 through an external network, such as the internet.

A user can interact with the server 500 to study the data received from a device 504, to review the analysis provided by the server 500, or to control the server's communication with local databases or local servers 518 or with the remote cloud 514. The user can interact with the server computer 500 directly or through the client device 516.

Although only one server computer 500 is illustrated in the example network communication architecture 502 depicted in FIG. 27, the network communication architecture 502 may include additional server computers 500 that are in communication with the devices 504 of the local mesh network 512. For example, the local server 518 can communicate with one or more of the devices 504. Communications between the local server 518 and the devices 504 can be pre-arranged (meaning that one or more devices 504 may be assigned to each of the local servers 518) or can be set and controlled by a user that has access to one or more of the local servers 518 (e.g., through the client device 516).

In some implementations, the server computer 500 manages the local mesh network 512. For example, the server computer 500 may determine the life-cycle of the local mesh network 512 (e.g., when to turn the local mesh network 512 on or off) or may determine which devices 504 have permission to join the local mesh network 512 at a current time or at a future time.

In a general communication protocol such as Thread, Zigbee, etc., an electronic device accesses a remote server on a cloud to use applications provided by the remote server. However, accessing a remote server (e.g., through the internet) can jeopardize the privacy of medical data. Although the local mesh network 512 can be implemented according to the features of a known communication protocol such as Thread, Zigbee, Bluetooth mesh, etc., the network communication architecture 500 disclosed herein provides distinguishable features from such general communication protocols. For example, while the local mesh network 512 can be implemented according to Thread protocol, unlike a Thread network, the present local mesh network 512 is not in a direct contact with remote servers (or clouds) and operates independently from the connections between the server computer 500 and any remote servers. In other words, the local mesh network 512 continues operating even if the server computer 500 is not in communication with any remote server or if such communication is lost. Similarly, the server computer 500 can continue its operations and communicate with other local servers 518 irrespective of its connection to the cloud 514. In these manners, full functionality of the workstation 100 can be maintained even if the internet connection of the medical facility is lost.

While the above-discussed configurable workstation 100 has been described and illustrated as including components with certain dimensions, sizes, shapes, materials, and configurations, and as being operated according to certain methods, in some embodiments a workstation that is otherwise substantially similar in structure and function to the above-discussed configurable workstation 100 may include one or more components with different dimensions, sizes, shapes, materials, and configurations or may be operated according to methods that include one or more different process flow steps. Additionally, in some embodiments, a workstation that is otherwise similar in construction and function to the above-discussed configurable workstation 100 may not include one or more of the above-discussed system components.

Figure 28:
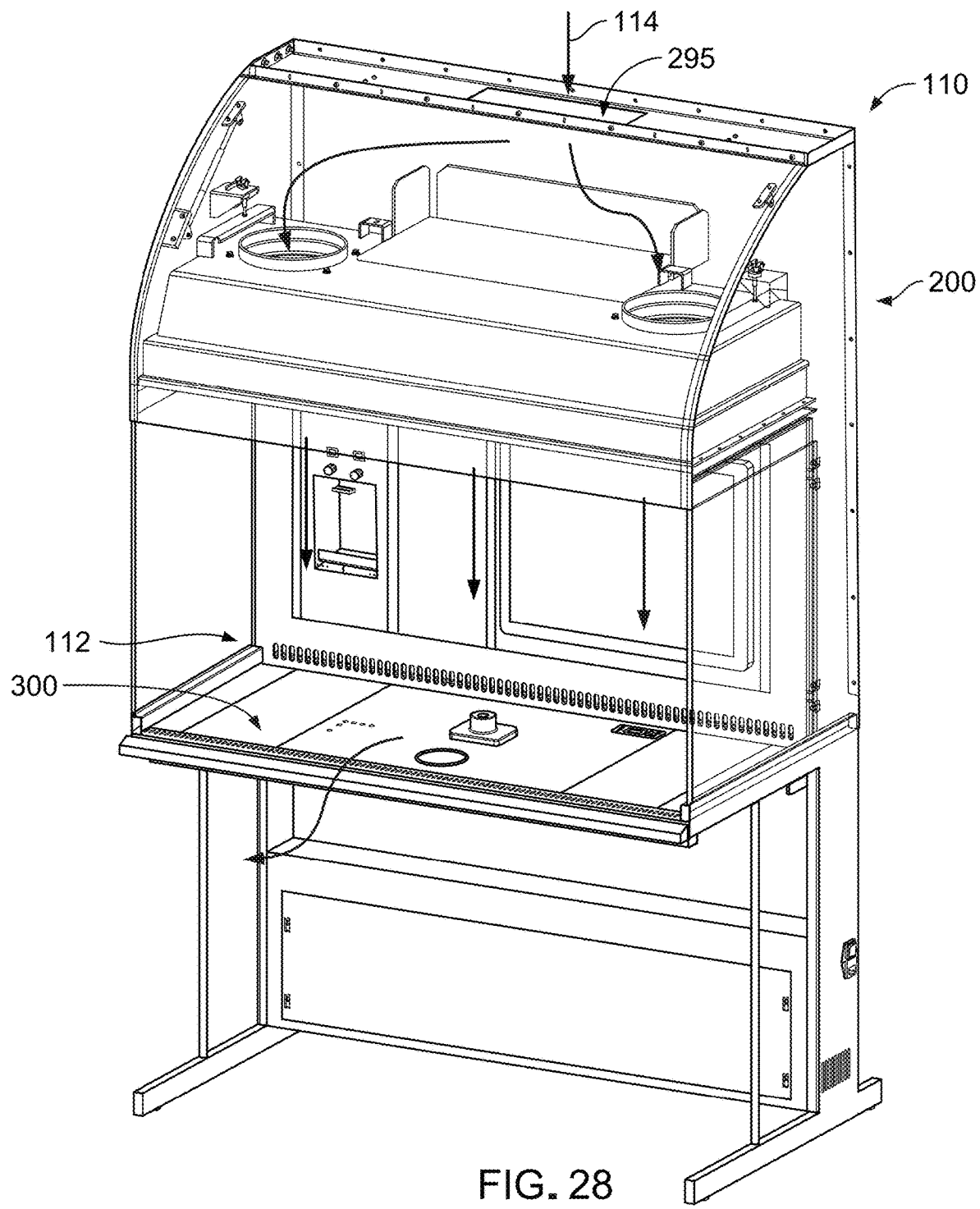
FIG. 28 illustrates an airflow path at a configurable workstation embodied as a Class I laminar flow cabinet.

For example, referring to FIG. 28, the air duct system 400 may be disassembled from the frame 200 of the configurable workstation 100 to convert the configurable workstation 100 from a Class II biosafety cabinet to a configurable workstation 110, which, is a Class I laminar flow cabinet (e.g., with or without any of the various modules 300). Accordingly, an airflow path 114 at the workstation 110 is designed to protect any specimens (e.g., product) handled in a workspace 112 from contaminants or other particulates present near the workstation 110, but not personnel working at the workstation 110 and an environment at which the workstation 110 is located.

Accordingly, the configurable workstation 110 includes all of the components of the configurable workstation 100 (e.g., the frame 200, the modules 300, and the server computer 500), except the air duct system 400 (e.g., the duct frame 402, the pressure chamber 406, the fan 408 enclosed therein, and the associated HEPA filter 410). Removal of the air duct system 400 changes a flow of the air from the airflow path 104 to the airflow path 114. Along the airflow path 114, the fans 260 within the pressure chamber 258 pull air from the surrounding environment through the opening 295 in the upper panel structure 202, through the HEPA filter 262, and into the workspace 112. Instead of being recirculated through the HEPA filter 262, the air instead flows out of the workspace 112 back into the surrounding environment.

The air duct system 400 may be reinstalled to the frame 200 to convert the configurable workstation 110 back into a Class II biosafety cabinet (e.g., back into the configurable workstation 100) as desired. As part of the installation, the duct frame 402 is sealed to inlets of the fans 268 (e.g., at the air ducts 404) and to the rear ends 296 of the slidable air duct 276 (e.g., at the rectangular openings 428). The platform 274 of the table 206 is also sealed to the slidable air duct 276 along the openings 288 and the lateral conduits 294.

Figure 29:
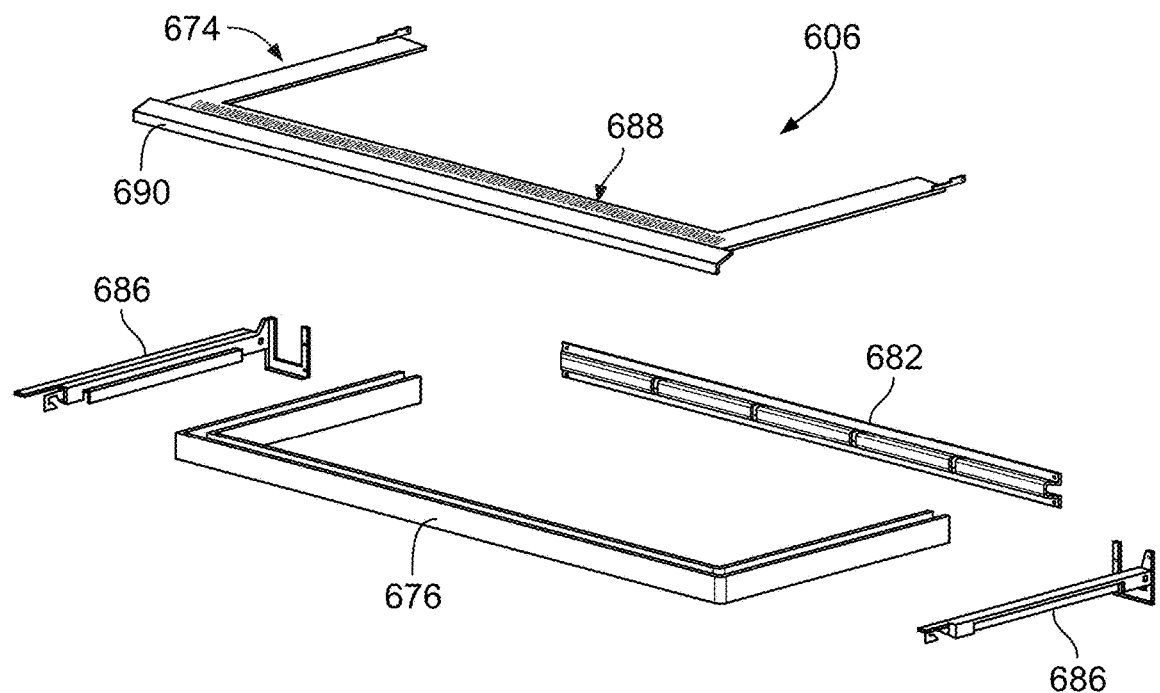
FIG. 29 is an exploded perspective view of a flip-top table that can be installed to a frame of the configurable workstation of FIG. 1.

While the configurable workstation 100 has been described and illustrated as including the table 206 that has a drawer-style configuration, in some embodiments, a configurable workstation that is otherwise substantially similar in construction and function to the configurable workstation 100 may alternatively include a table with a flip-top configuration. For example, referring to FIG. 29, a table 606 includes an air duct 676 and a platform 674 that can be flipped upward (e.g., pivoted from a rear end) from the air duct 676 to allow access to the air duct 676 for cleaning and sterilization of the air duct 676. The platform 674 defines a front row of openings 688 to allow air to pass into the air duct 676 and a handle 690 for manipulating the platform 674. The table 606 also includes a rear bracket 682 and two lateral brackets 686 for installation of the table 606 to the frame 200 and support of the air duct 676.

Figure 30:
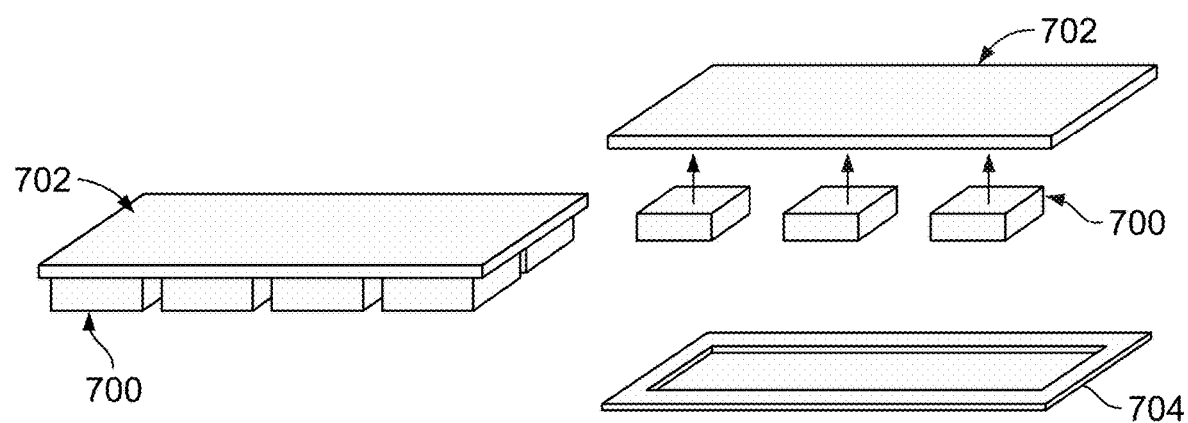
FIG. 30 is a perspective view of module leveling and gap sealing using a protector film.
Figure 31:
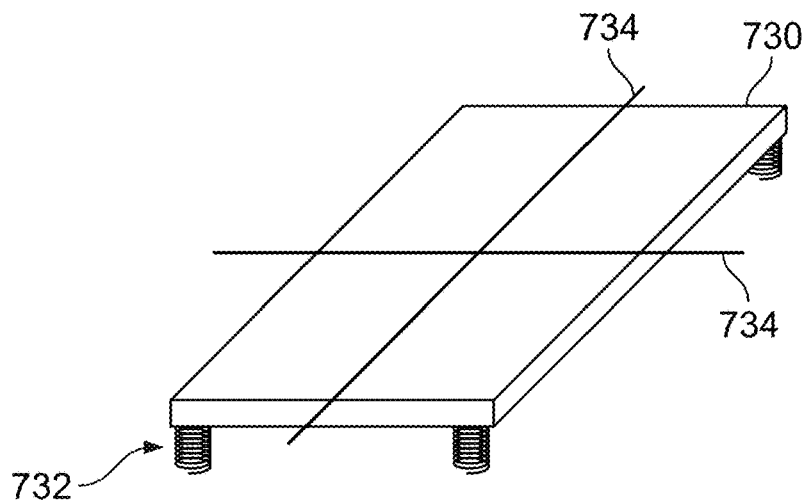
FIG. 31 is a perspective view of module leveling using spring-like components that push a module up against multiple level rails.

While the modules 300 have been described and illustrated as being leveled using counter-directed push and pull mechanisms and sealed using gaskets, in some embodiments, a configurable workstation and modules that are otherwise substantially similar in construction and function to the configurable workstation 100 and the modules 300 may be designed for different types of module leveling and gap-sealing. For example, referring to FIG. 30, in some embodiments, a protector film 702 may be installed atop modules 700 to cover any gaps present between the modules 700, which may themselves be supported by a table platform 704. The protector film 702 also provides a flat work surface atop the modules 700. In some embodiments, as shown in FIG. 31, a module 730 may be equipped with springs or spring-like components 732 that push the module 730 up against one or more flat, level rails 734 or a surface to level the module 730.

Figure 32:
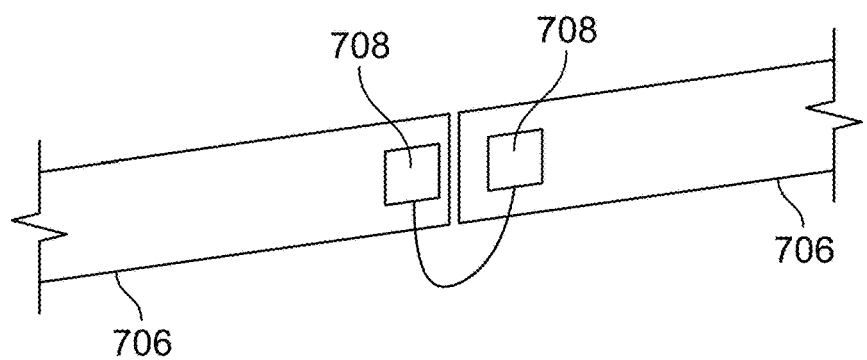
FIG. 32 is a side view of magnets used to pull two modules toward each other for gap minimization.
Figure 33:
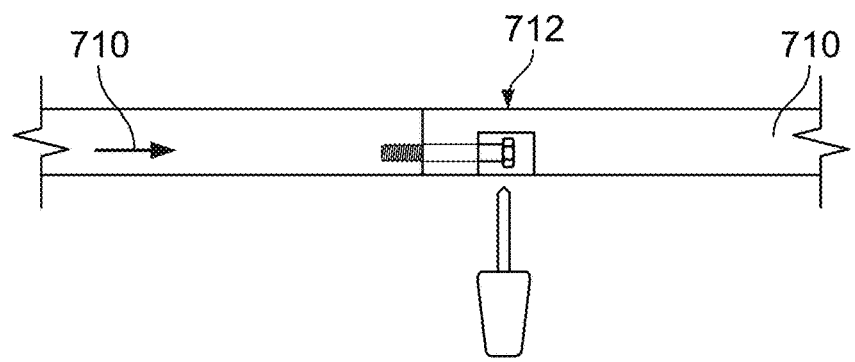
FIG. 33 is a side view of a cam lock screw mechanism used to pull two modules toward each other for gap minimization.
Figure 34:
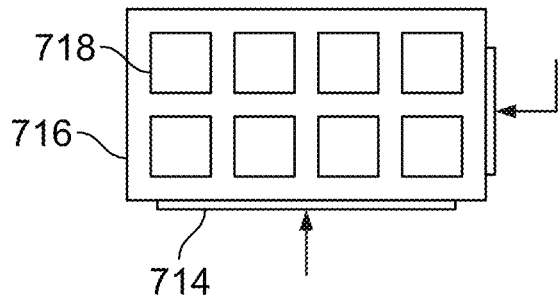
FIG. 34 is a top view of a workstation frame designed to apply lateral pressure to a table at which modules are installed to minimize gaps between the modules.
Figure 35:
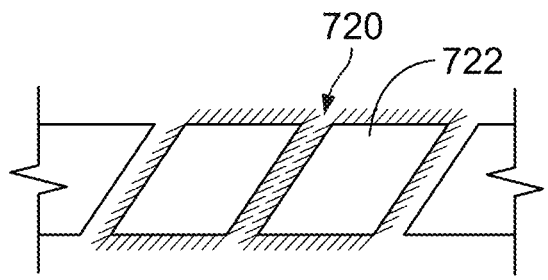
FIG. 35 is a perspective view of liquid gasket applied between modules to fill gaps between the modules.
Figure 36:
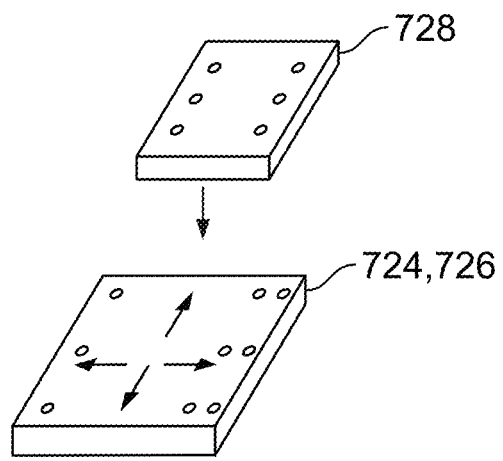
FIG. 36 is an exploded perspective view of a module that can be compressed with an accessory tool to expand laterally toward adjacent modules to minimize gaps therebetween.

In some embodiments, as shown in FIG. 32, modules 706 may be equipped with magnets 708 that pull the modules 706 towards each other laterally to minimize gaps between the modules 706. In some embodiments, as shown in FIG. 33, modules 710 may be connected to each other with one or more cam lock screw mechanisms 712 to minimize gaps between the modules 710. In some embodiments, as shown in FIG. 34, a workstation frame 714 may be designed to apply lateral pressure to a table 716 at which modules 718 are installed to minimize gaps between the modules 718. In some embodiments, as shown in FIG. 35, liquid gasket 720 can be applied between modules 722 and subsequently cured to fill gaps between the modules 722 and provide a smooth transition surface between the modules 722. In some embodiments, as shown in FIG. 36, a module 724 may include a housing 726 formed of a plastic material such that the housing 726 is flexible. Such housing 726 can be compressed with an accessory tool 728 to expand laterally towards adjacent modules 724 to minimize gaps therebetween.

Figure 37:
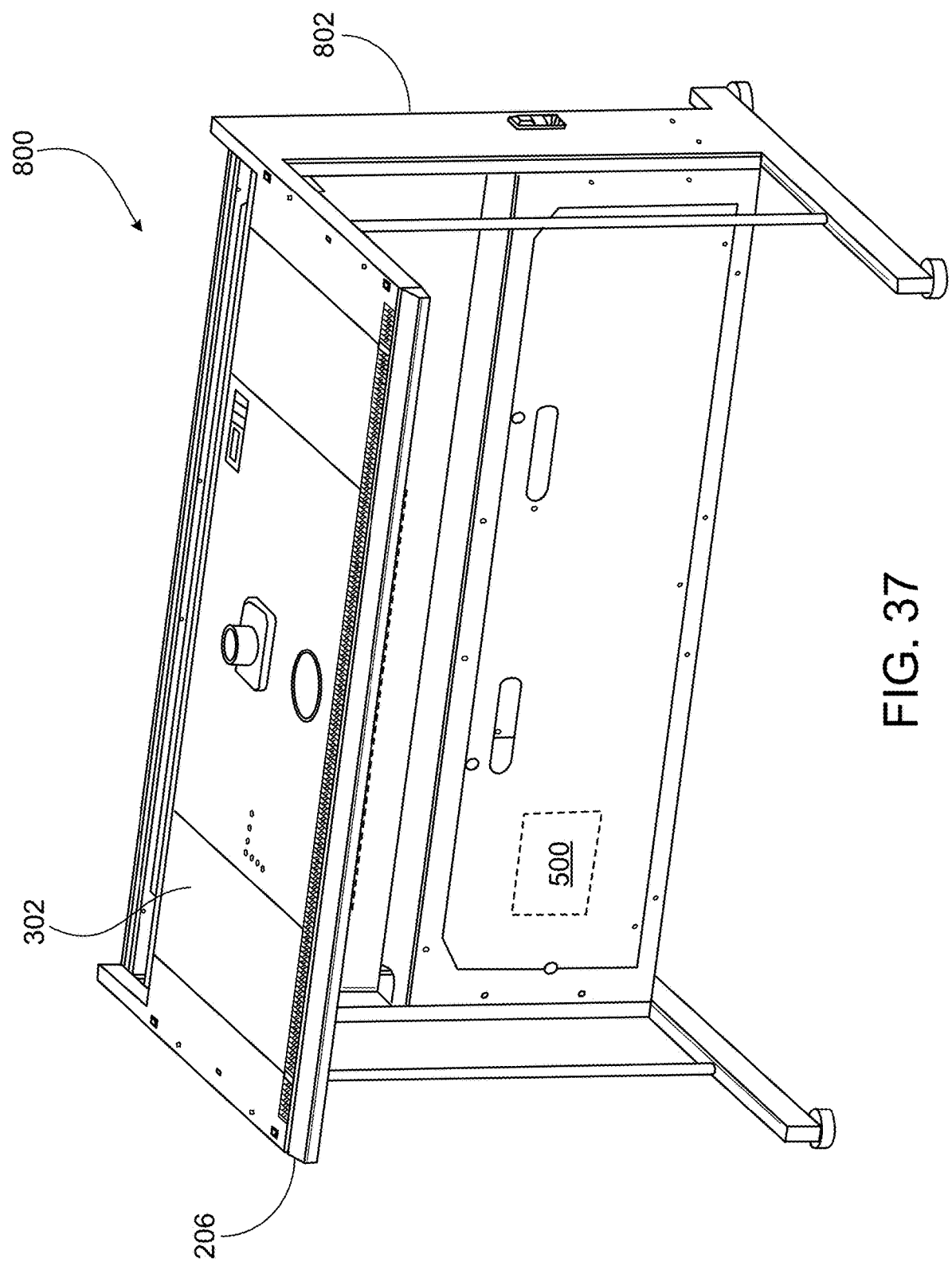
FIG. 37 is a perspective view of a configurable workstation embodied as a no-hood frame.
Figure 38:
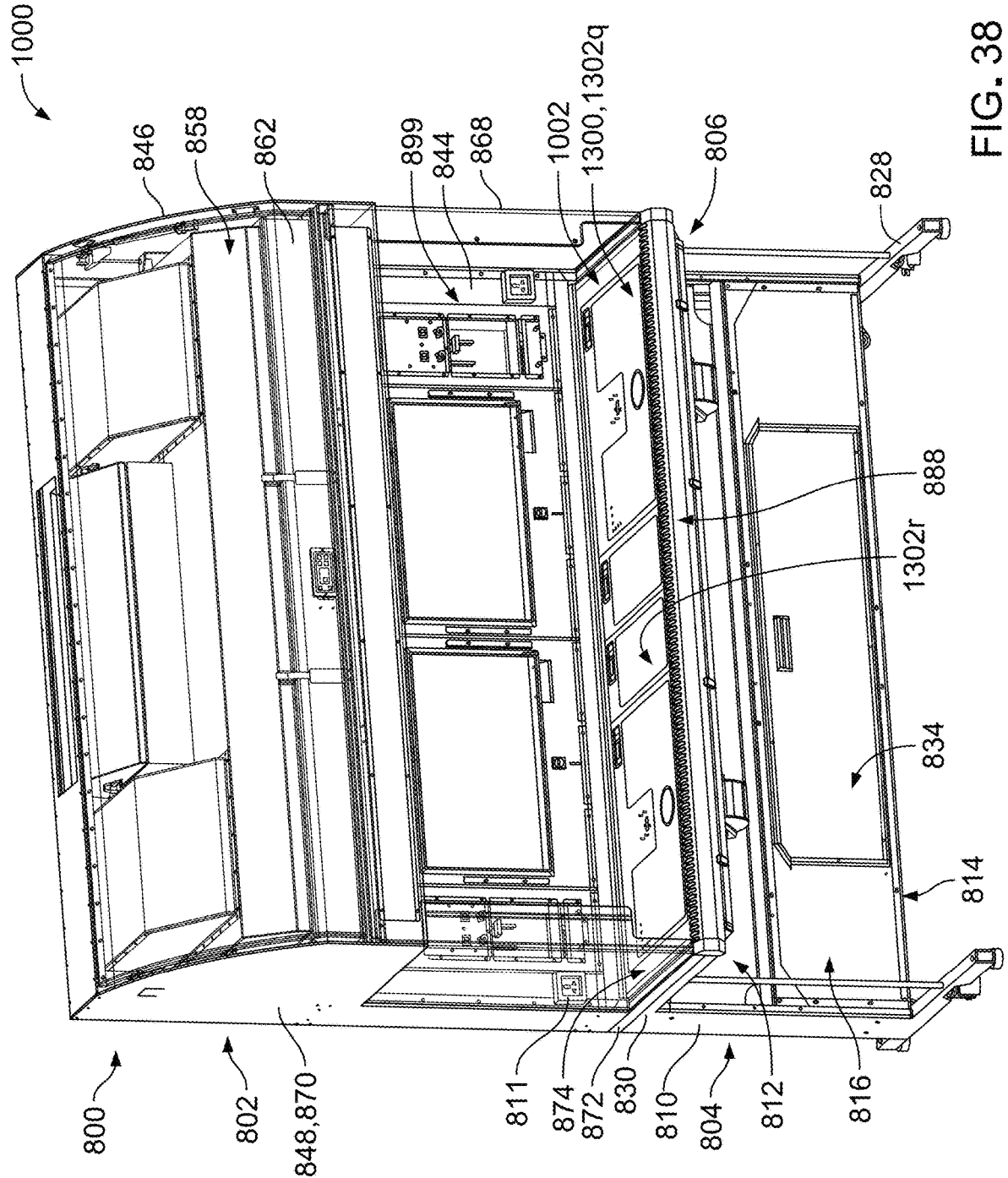
FIG. 38 is a front perspective view of a configurable workstation.
Figure 39:
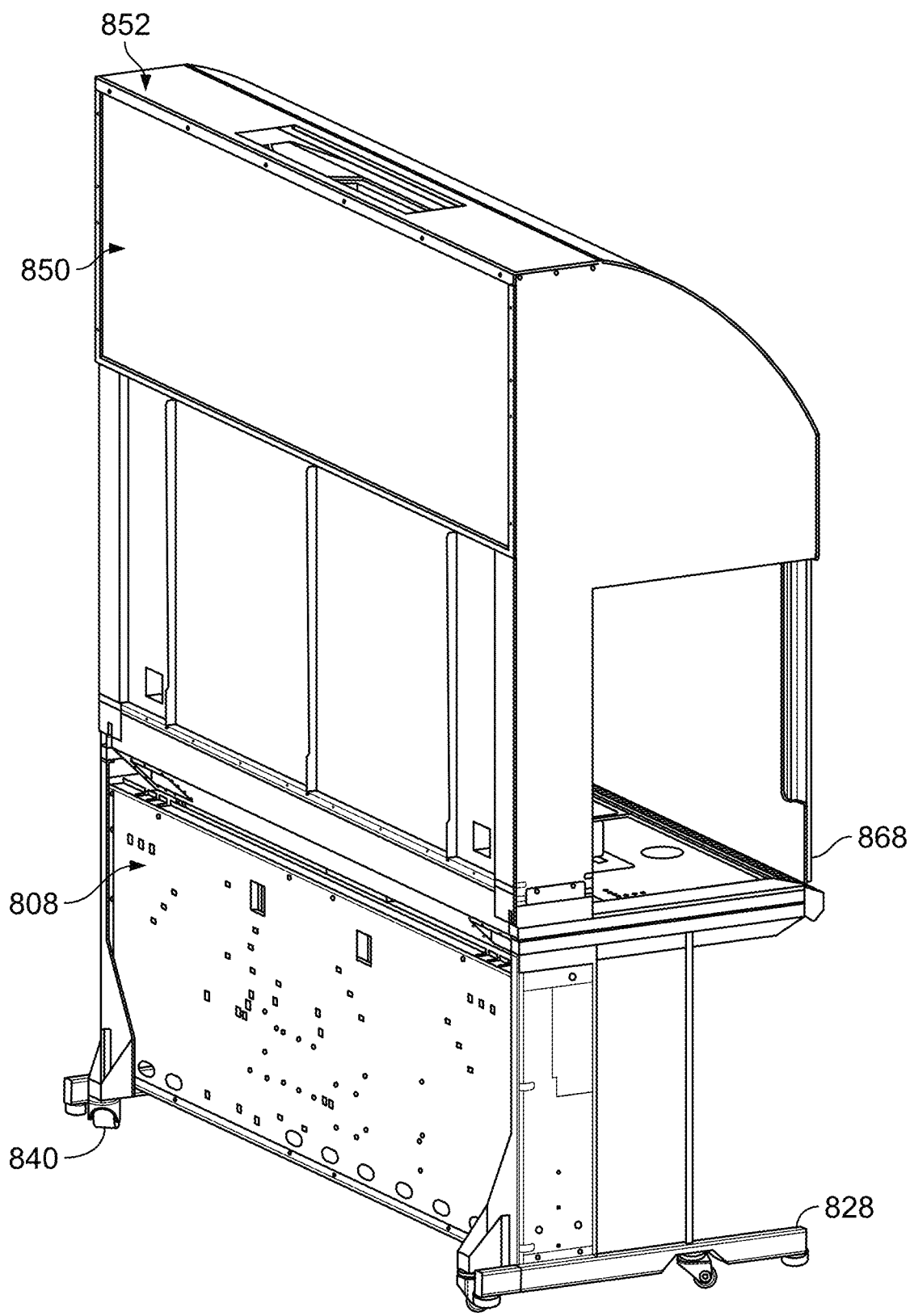
FIG. 39 is a rear perspective view of the configurable workstation of FIG. 38.
Figure 40:
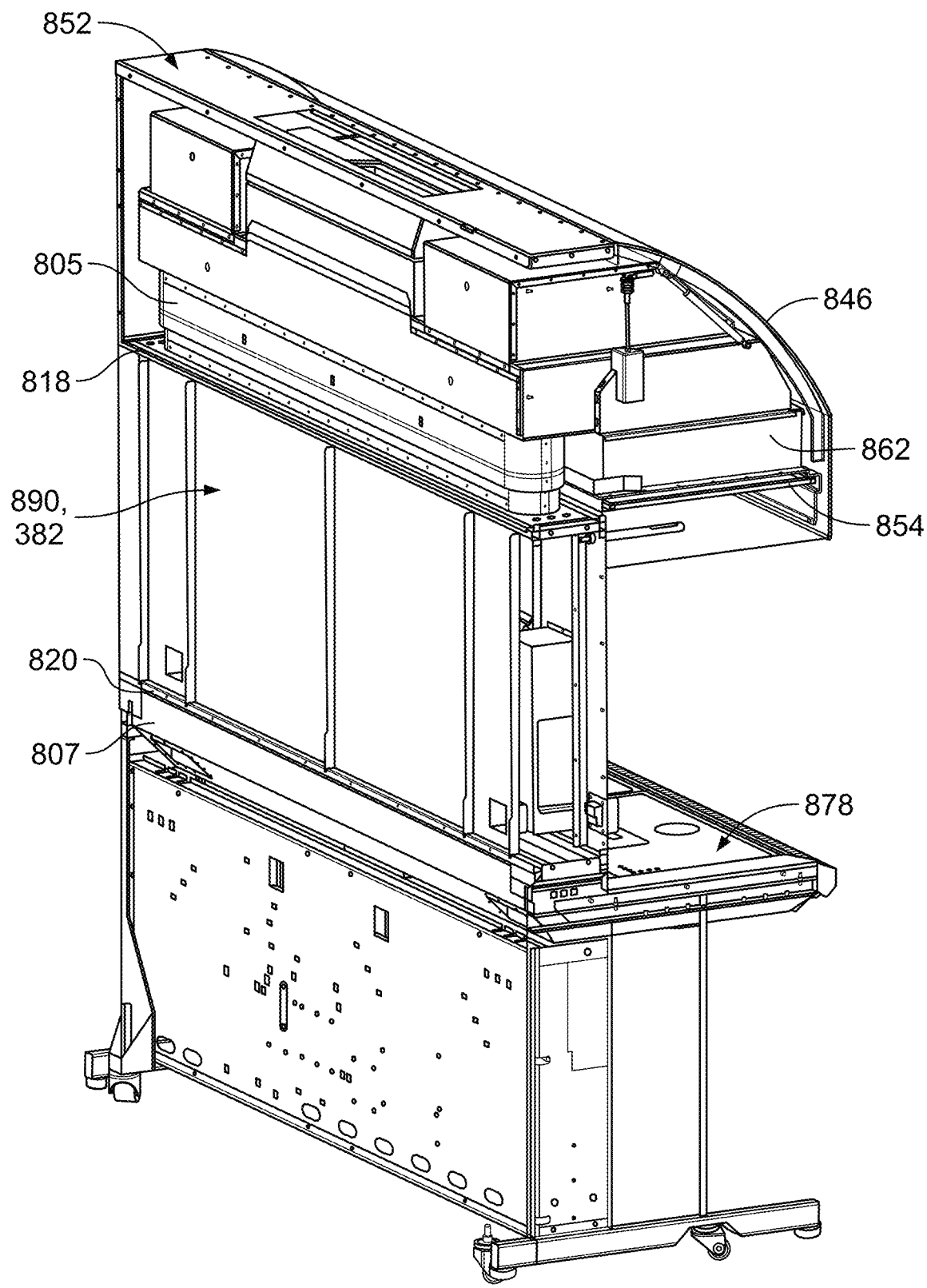
FIG. 40 is a rear perspective view of the configurable workstation of FIG. 38, with certain frame panels removed to expose internal components.

In some embodiments, the configurable workstation 100 may be converted from a Class II biosafety cabinet into a no-hood frame that includes the lower panel structure 204 of the frame 200, the table 206, and any table-top modules 302 installed to the table 206, but does not include the upper panel structure 202 of the frame 200, any wall modules 304, or the air duct system 400. FIG. 37 illustrates such a configurable workstation 800, which includes a frame 802, the server computer 500, the table 206, and a selection of table-top modules 302. The frame 802 is substantially similar in construction and function to the lower panel structure 204 of the frame 200.

While the configurable workstation 100 has been described and illustrated with a configuration in which the server computer 500 is located at the frame 200, in some embodiments of the configurable workstation 100 and the configurable workstation 1000 discussed below, the server computer 500 may be located elsewhere, such as at a location generally near the configurable workstation, but without being installed to the frame. In some embodiments, the server computer 500 may be located at a location relatively remote from the configurable workstation. In some embodiments, the server computer 500 may be provided to a user as a separate module and then installed to the frame by the user onsite.

In some embodiments, a configurable workstation may be designed to circulate air along a flow path that is different from either of the air flow paths 104, 114 described above with respect to the configurable workstation 100. For example, FIGS. 38-45 illustrates such a configurable workstation 1000 that provides an alternative airflow path 1004. With the exception of components and component arrangements that differentiate the airflow path 1004 from the airflow paths 104, 114, the configurable workstation 1000 is otherwise substantially similar in construction and function to the configurable workstation 100. Accordingly, the configurable workstation 1000 is a networked biosafety cabinet that provides a workspace 1002 for carrying out any of the above-mentioned biological protocols in a laboratory environment. Additionally, the configurable workstation 1000 has a modularized design that is customizable on-site at a laboratory to meet any of the various laboratory requirements discussed above and to provide needed functional capabilities. The configurable workstation 1000 therefore includes a frame 800, multiple modules 1300 that may be selectively installed to the frame 800 as desired for customizing a functional profile of the configurable workstation 1000, and the server computer 500, which implements a web application to provide a central user interface for communicating with the configurable workstation 1000.

The frame 800 is generally similar in structure and function to the frame 200 and includes an upper panel structure 802, a lower panel structure 804, and a table 806 that extends horizontally from the upper and lower panel structures 802, 804. The lower panel structure 804 includes a rear panel 808, two lateral panels 810, a front panel 812, and a lower panel 814 that together define an enclosure 816 that houses various components of the configurable workstation 1000. The lower panel structure 804 further includes inner and outer lower rails that together form feet 828 that support the weight of the configurable workstation 1000. The feet 828 are equipped with wheels 840 for optionally rolling the configurable workstation 1000. The lower panel structure further includes inner and outer upper rails that together form upper support beams 830 that in part support the table 806.

The front panel 812 is equipped with multiple power outlets 232 at which any of the modules 1300 or other accessory devices can be powered at the configurable workstation 1000. The enclosure 816 houses several components that are accessible via a service panel 834. For example, the enclosure 816 houses a control module 236 that includes a PCB 238 on which the server computer 500 is implemented, a power supply 240 that powers the configurable workstation 1000, and a power switch module 242 that manages distribution of the power (e.g., such components are illustrated in FIG. 3 with respect to the configurable workstation 100).

The upper panel structure 802 includes a front panel 844 defining an opening 899 at which various modules 1300 can be installed, a front cover 846, and two lateral panels 848. The opening 899 of the front panel 844 has a rectangular shape to accommodate selected modules 1300. The opening 899 typically has a width of about 1.0 m to about 2.0 m and a height of about 0.4 m to about 0.7 m (e.g., 1.08 m in the case of a 4-foot wide frame 800 or 1.67 m in the case of a 6-foot wide frame 800). The front panel 844 is also equipped with two oppositely located electrical outlets 811. The upper panel structure 802 also includes a rear panel 850, an upper panel 852, and a lower panel 854 that together define an enclosure 856 (e.g., a workstation hood) housing various components that are operable to effect air flow at the configurable workstation 1000. The lower panel 854 is also equipped with lights that can illuminate the workspace 1002. The upper panel structure 802 further includes a lower air duct 807 that extends horizontally across the frame 800.

The enclosure 856 is equipped with a pressure chamber 858 housing two sets of oppositely located fans 860, 897 that operate in parallel to provide downward airflow within the frame 800, a HEPA filter 862 located below the pressure chamber 858 for filtering air flowing downward into the workspace 1002, and a HEPA filter 803 for filtering air that flows out of the frame 800. The enclosure 856 also houses triangular brackets 892 for mounting of the fans 860, 897 to the pressure chamber 858. The enclosure 856 is also equipped with an upper air duct 805 that extends horizontally across the enclosure 856 adjacent the rear panel 850. The front cover 846 is openable (e.g., pivotable at the upper panel 852) to switch out the HEPA filter 862 as needed, and the pressure chamber 858 as openable (e.g., pivotable below the upper panel 852) to switch out the HEPA filter 803 as needed.

The upper panel structure 802 further includes lateral panels 868 that in part define the workspace 1002 of the configurable workstation 1000. The lateral panels 868 are transparent or translucent and therefore provide lateral viewing windows for the workspace 1002. Example materials from which the lateral panels 868 may be made include glass, acrylic, or other types of transparent plastic. The lateral panels 848 define upper panel regions 870 that laterally close off the enclosure 856 and lower support beams 872 that in part provide support for the table 806.

The table 806 of the frame 800 includes two side walls 876 that extend forward from the lower air duct 807 and a platform 874 that extends horizontally between the two side walls 876. The platform 874 defines a rectangular opening 878 at which various modules 1300 can be installed to form a flat work surface within the workspace 1002. The opening 878 typically has a width of about 1.0 m to about 2.0 m (e.g., 1.05 m in the case of a 4-foot wide frame 800 or 1.7 m in the case of a 6-foot wide frame 800) and a depth of about 0.4 m to about 0.6 m.

The platform 874 rests atop the side walls 876 and wraps around the side walls 876 along a front edge of the table 806. The table 806 also includes a support rail 864 that extends along a lower edge of the platform 874 and between the side walls 876. The support rail 864 is secured to the platform 874 with fasteners 809. The table 806 further includes an inner rear bracket 882 and an inner front bracket 884 to which the modules 1300 can be attached. The platform 874 also defines a frontal row of elongate openings 888 through which air in the workspace 1002 can flow towards the lower air duct 807. Air can also flow into the lower air duct 807 through an elongate gap 886 defined between and along rear edges of the platform 874 and the lower air duct 807.

The frame 800 is a rigid structure that typically has a total height of about 1.8 m to about 3.0 m, a total width of about 1.0 m to about 2.0 m, and a total depth of about 0.5 m to about 1.0 m. The various components of the frame 800 (e.g., including the upper panel structure 802, the lower panel structure 804, and the table 806) are typically made of one or more materials that can chemically withstand various laboratory cleaning substances. Example materials from which the frame 800 may be made include steel, aluminum, glass, and plastic. The frame 800 (e.g., excluding the modules 1300) typically weighs about 350 lbs to about 1200 lbs.

The modules 1300 are identical in construction and function to any of the modules 300, 700, 710, 718, 722, 724, 730, except that the modules 1300 are additionally equipped with separate wall panels. For example, each module 1300 may be embodied as a table-top module 302 that is provided with a lower wall panel 380 or as a wall module 304 that is provided with a rear wall panel 382. All of the lower wall panels 380 together form a lower wall 880 of the table 806, while all of the rear wall panels 382 together form a rear frame wall 890 of the upper panel structure 802. The wall panels 382 are attached at upper ends to a platform 818 of the upper air duct 805 and attached at lower end to a support rail 820 positioned along the lower air duct 807. The wall panels 380 are secured to the support rail 864 at front ends and to lower air duct 807 at rear ends. The modules 1300 may be installed to the table 806 at the inner brackets 882, 884 with one or more of any of the installation mechanisms and features described above with respect to FIGS. 17-26. In the example configurable workstation 1000, the table-top modules 1300 include two microscope modules 1302$q$ formed to support a microscope for viewing a specimen and two heating plates 1302$r$ with RFID capability, while the wall modules 1300 include two humidity modules 1302$s$ and two monitors 1302$t$.

Figure 41:
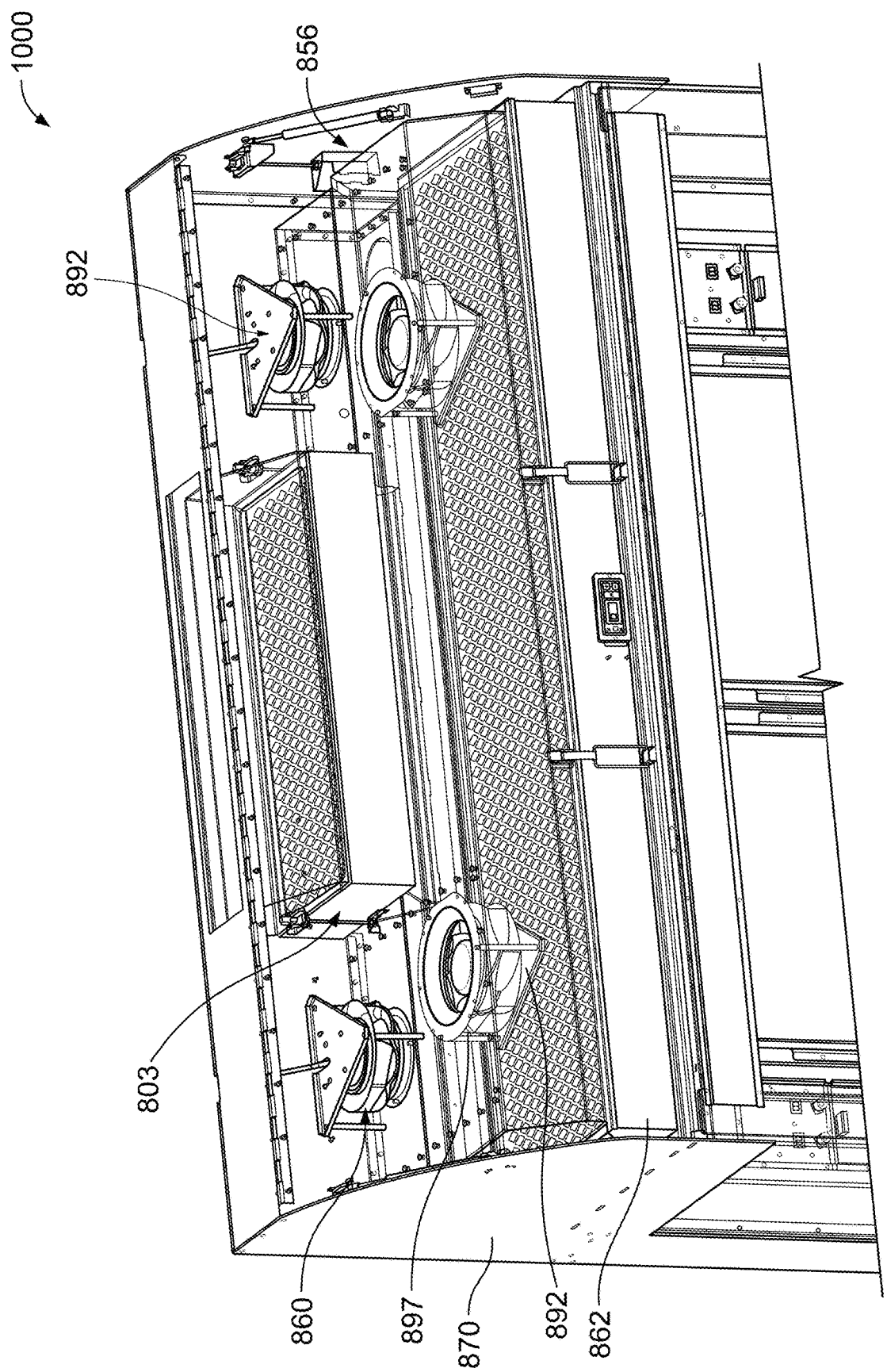
FIG. 41 is an enlarged perspective view of an airflow enclosure of the configurable workstation of FIG. 38.
Figure 42:
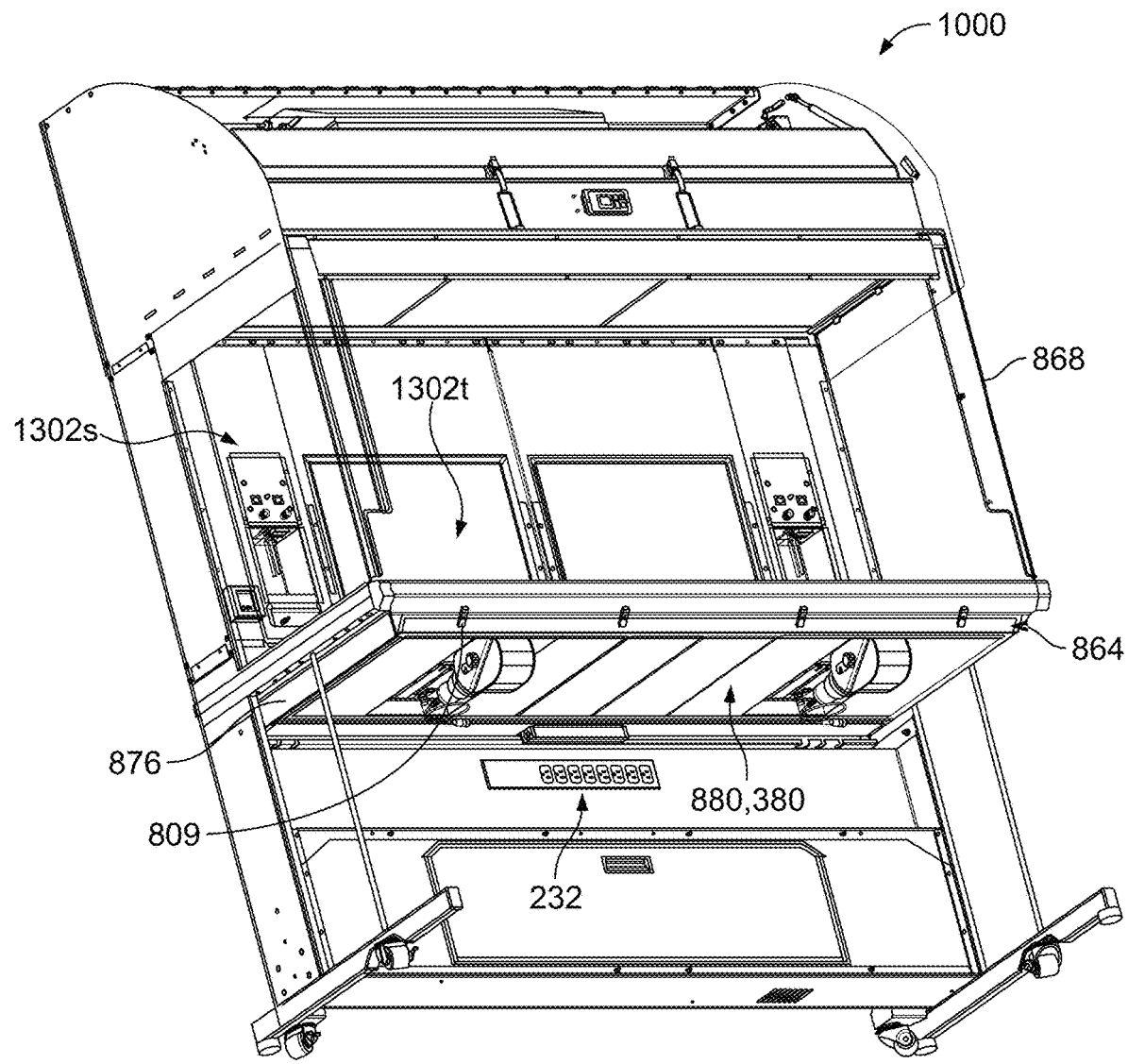
FIG. 42 is a bottom perspective view of the configurable workstation of FIG. 38.
Figure 43:
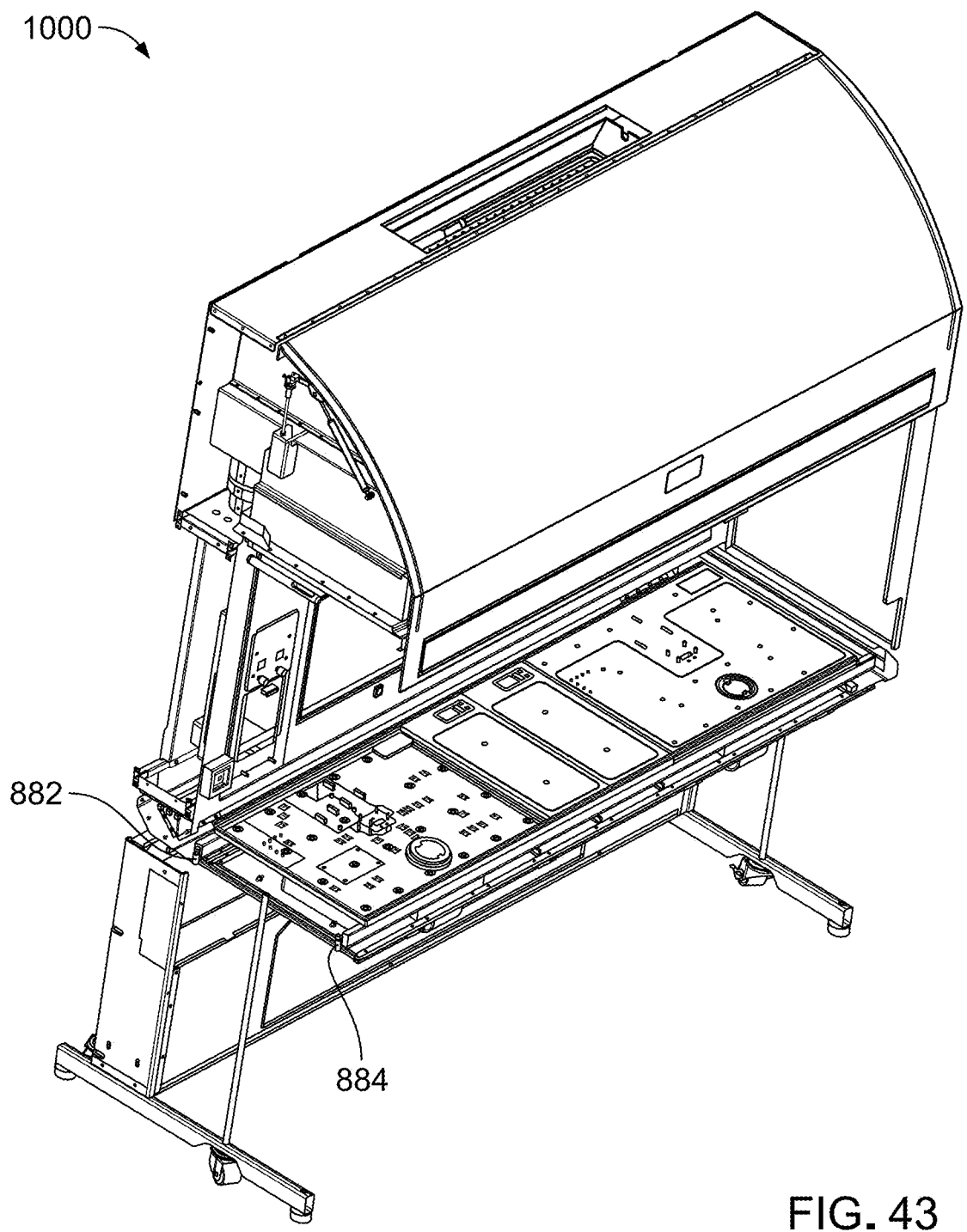
FIG. 43 is a top perspective view of the configurable workstation of FIG. 28, with certain frame panels removed to expose internal components.
Figure 44:
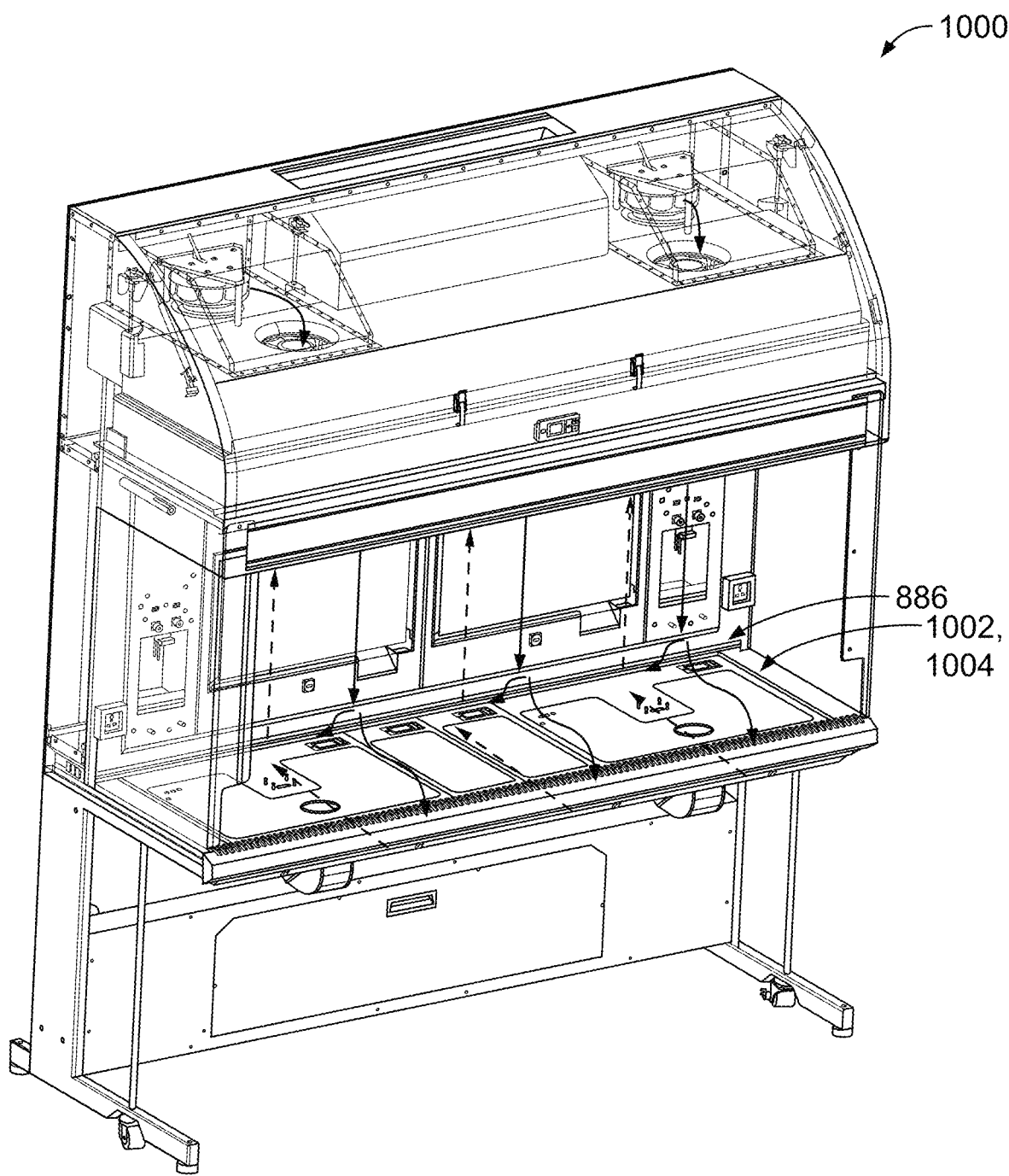
FIG. 44 illustrates an airflow path at the configurable workstation of FIG. 38 from a front perspective.
Figure 45:
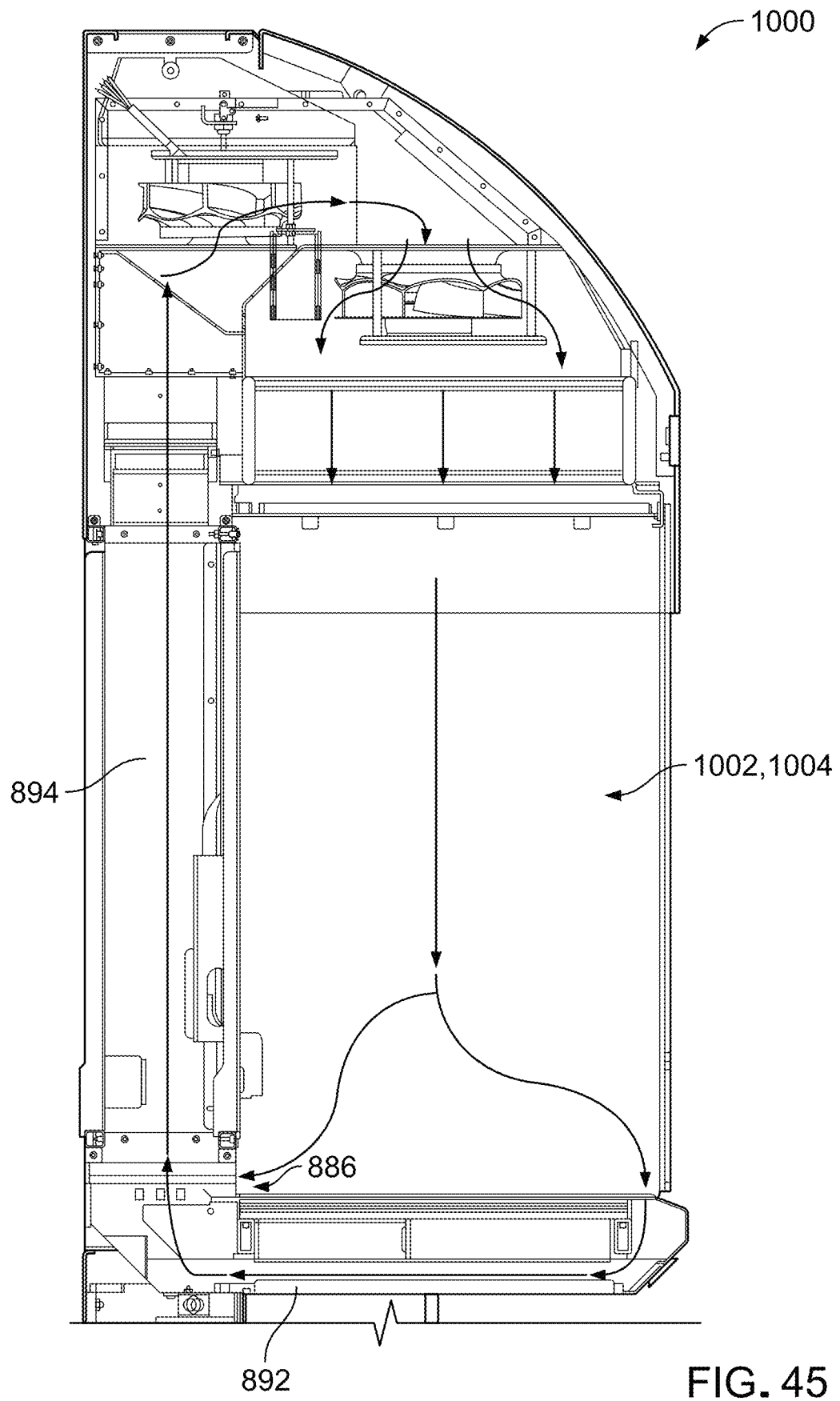
FIG. 45 illustrates an airflow path at the configurable workstation of FIG. 38 from a side view.

Referring to FIGS. 41, 44 and 45, the workstation 1000 is embodied as a Class II biosafety cabinet (e.g., with or without any of the illustrated modules 1300), such that an airflow path 1004 at the workstation 1000 is designed to protect personnel working at the workstation 1000, an environment at which the workstation 1000 is located, and any specimens handled in the workspace 1002 from contaminants or other particulates present near the workstation 1000. Accordingly, the fans 860, 897 within the pressure chamber 858 recirculate air within the workspace 1002 along the airflow path 1004 by flowing the air beneath the platform 874 of the table 806 and back through the HEPA filter 862 before the air reenters the workspace 1002. The airflow path 1004 passes through an interior compartment 892 of the table 806 and an interior compartment 894 of the upper panel structure 802.

For example, air within the workspace 1002 is circulated in a downward direction and then rearwardly into the gap 886, where the air passes into the lower air duct 807. Air within the workspace 1002 is also circulated forwardly into the openings 888 of the platform 874, where the air passes into the interior compartment 892 of the table 806 and then flows into the lower air duct 807. Air within the lower air duct 807 is circulated upward through the interior compartment 894, drawn into the upper air duct 805, and driven downward by the fans 860, 897 through the HEPA filter 862 to remove any harmful particles or contaminants before reentering the workspace 1002. Thus, the fans 860, 897 circulate air along the airflow path 1004 through the workspace 1002, the table 806, and the upper panel structure 802 to meet certain Class II requirements. Serial positioning of two fans (e.g., an upper fan 860 that circulates air to a lower fan 897) reduces a total volume of noise generated by the flow of air at the enclosure 856, as compared to an arrangement that includes only a single fan for air circulation through a workspace.

Other embodiments are also within the scope of the following claims.

What is claimed is:

1. A configurable workstation comprising:
a support frame comprising a workspace for performing a scientific procedure;
a plurality of modules, wherein each module of the plurality of modules is configured to be installed to the support frame for customizing a functional profile of the configurable workstation; and
a server computer hosting an application, wherein the server computer is configured to communicate with one or more remote devices on a cloud network via an external network, and wherein the application is configured to provide a user interface for controlling operations of the configurable workstation.

2. The configurable workstation of claim 1, wherein the plurality of modules comprises a plurality of table-top modules that are configured to be oriented horizontally at the support frame and a plurality of wall modules that are configured to be oriented vertically at the support frame.

3. The configurable workstation of claim 2, wherein the support frame comprises a table at which each of one or more table-top modules of the plurality of table-top modules is configured to be installed to provide a substantially flat work surface at the workspace and a wall at which each of one or more wall modules of the plurality of wall modules is configured to be installed, thereby forming a vertical boundary of the workspace.

4. The configurable workstation of claim 3, wherein the table comprises a platform comprising an opening sized to receive the one or more table-top modules and rails to which the one or more table-top modules are attachable for installation to the frame.

5. The configurable workstation of claim 4, wherein each table-top module of the plurality of table-top modules comprises a housing that is attachable to the rails, and wherein the table-top module is equipped with one or more fasteners configured for pushing the table-top module up away from the rails to level the table-top module with respect to the platform and any adjacent table-top modules installed at the table to provide the flat work surface.

6. The configurable workstation of claim 5, wherein the one or more fasteners are one or more first fasteners, and wherein the table-top module is further equipped with one or more second fasteners configured for pulling the table-top module downward towards the rails to lock the table-top module in a lateral position at the table.

7. The configurable workstation of claim 4, further comprising a gasket that is configured to seal a gap between the table-top module and an adjacent table-top module.

8. The configurable workstation of claim 3, wherein the wall comprises an opening sized to receive the one or more wall modules.

9. The configurable workstation of claim 8, further comprising a gasket that is configured to seal a gap between adjacent wall modules of the one or more wall modules installed at the vertical opening.

10. The configurable workstation of claim 2, wherein the plurality of table-top modules comprises one or more of an anti-vibration platform, an incubator, a cooling unit, one or more heating plates, a microscope module, and a blank table platform.

11. The configurable workstation of claim 10, wherein the plurality of wall modules comprises one or more of a humidifier, an ICSI arch, a wall tunnel, one or more monitors, a power outlet panel, and a blank wall panel.

12. The configurable workstation of claim 11, wherein one or more of the plurality of modules comprise an RFID capability for tracking a specimen handled at the configurable workstation.

13. The configurable workstation of claim 1, wherein the support frame and the plurality of modules comprise multiple medical devices that are subject to regulatory review.

14. The configurable workstation of claim 13, wherein the user interface is a first user interface, and wherein each medical device of the multiple medical devices comprises equipment for carrying out a dedicated medical function, a power port, hardware, firmware, a second user interface, and a network communication board for communicating with the server computer.

15. The configurable workstation of claim 14, wherein the multiple medical devices are configured to communicate with each other and with the server computer via a local network.

16. The configurable workstation of claim 15, wherein the local network comprises a mesh network.

17. The configurable workstation of claim 14, wherein each medical device of the multiple medical devices is configured to be powered and operated independently of other medical devices of the multiple medical devices.

18. The configurable workstation of claim 1, wherein the support frame comprises a table providing a work surface at the workspace and a wall that forms a vertical boundary of the workspace.

19. The configurable workstation of claim 18, wherein the table comprises a platform comprising a plurality of horizontal openings along a front edge of the platform and an air chamber positioned underneath the platform.

20. The configurable workstation of claim 19, wherein the support frame comprises an air duct positioned along a rear edge of the platform, and wherein a gap is formed between the rear edge of the platform and the air duct.

21. The configurable workstation of claim 20, wherein the air duct is in fluid communication with the plurality of horizontal openings and the gap.

22. The configurable workstation of claim 20, wherein the air duct is a first air duct, and wherein the support frame further comprises a second air duct that is positioned above and in fluid communication with the first air duct.

23. The configurable workstation of claim 19, further comprising:
one or more fans disposed above the workspace and configured to circulate air downward into the workspace; and
a filter disposed beneath the one or more fans for filtering the air that flows from the one or more fans.

24. The configurable workstation of claim 23, wherein the one or more fans comprise two fans arranged in serial in an airflow path.

25. The configurable workstation of claim 23, wherein the configurable workstation is configured to flow air along a recirculation airflow path downward from the one or more fans, into the workspace, underneath the platform of the table, upwardly behind the wall, and back to the one or more fans.

26. The configurable workstation of claim 23, further comprising one or both of an exhaust fan and a vent for exhausting air from an interior region of the support frame to an ambient environment.

27. The configurable workstation of claim 1, further comprising an air duct system that is configured to be installed to the support frame for changing an airflow path at the configurable workstation.

28. The configurable workstation of claim 27, wherein the air duct system is removable from the support frame to allow air to be circulated downward into the workspace by the one or more fans along a flow-through airflow path.

29. The configurable workstation of claim 27, wherein the configurable workstation is convertible between a Class II biosafety cabinet and a Class I laminar flow cabinet.

30. The configurable workstation of claim 2, wherein the support frame comprises:
an upper panel structure that forms the workspace;
a lower panel structure that supports the upper panel structure; and
a table that extends intermediately between the upper and lower panel structures and that provides a work surface at the workspace.

31. The configurable workstation of claim 30, wherein the upper panel structure is configured to support one or more of the plurality of wall modules, and wherein the table is configured to support one or more of the plurality of table-top modules.

32. The configurable workstation of claim 1, wherein the server computer is housed at the support frame.

33. The configurable workstation of claim 1, wherein the server computer is configured to communicate with one or more client devices and with one or more local servers via a wired or wireless local area network (LAN).

34. The configurable workstation of claim 1, wherein the scientific procedure is part of an IVF protocol.

35. A configurable workstation comprising:
a support frame comprising a workspace for performing a scientific procedure;
a plurality of modules, wherein each module of the plurality of modules is configured to be installed to the support frame for customizing a functional profile of the configurable workstation; and
a server computer hosting an application, wherein the application is configured to provide a first user interface for controlling operations of the configurable workstation,
wherein the support frame and the plurality of modules comprise multiple medical devices that are subject to regulatory review,
wherein each medical device of the multiple medical devices comprises equipment for carrying out a dedicated medical function, a power port, hardware, firmware, a second user interface, and a network communication board for communicating with the server computer, and
wherein the multiple medical devices are configured to communicate with each other and with the server computer via a network.

36. The configurable workstation of claim 35, wherein the plurality of modules comprises a plurality of table-top modules that are configured to be oriented horizontally at the support frame and a plurality of wall modules that are configured to be oriented vertically at the support frame.

37. The configurable workstation of claim 35, further comprising an air duct system that is configured to be installed to the support frame for changing an airflow path at the configurable workstation.

38. The configurable workstation of claim 35, wherein the server computer is configured to communicate with one or more client devices and with one or more local servers via a local area network (LAN).

39. A configurable workstation comprising:
a support frame comprising:
a workspace for performing a scientific procedure,
a wall that forms a vertical boundary of the workspace, and
a table that provides a work surface at the workspace, wherein the table comprises a platform comprising a plurality of horizontal openings along a front edge of the platform and an air chamber positioned underneath the platform;
one or more fans disposed above the workspace and configured to circulate air downward into the workspace;
a filter disposed beneath the one or more fans for filtering the air that flows from the one or more fans, wherein the configurable workstation is configured to flow air along a recirculation airflow path downward from the one or more fans, into the workspace, underneath the platform of the table, upwardly behind the wall, and back to the one or more fans;
a plurality of modules, wherein each module of the plurality of modules is configured to be installed to the support frame for customizing a functional profile of the configurable workstation; and
a server computer hosting an application, wherein the application is configured to provide a user interface for controlling operations of the configurable workstation.

40. A configurable workstation comprising:
a support frame comprising a workspace for performing a scientific procedure;
a plurality of modules, wherein each module of the plurality of modules is configured to be installed to the support frame for customizing a functional profile of the configurable workstation; and
a server computer hosting an application, wherein the application is configured to provide a first user interface for controlling operations of the configurable workstation,
wherein the server computer is configured to communicate with one or more client devices and with one or more local servers via a wired or wireless local area network (LAN).

* * * * *